United States Patent [19]
Peery et al.

[11] Patent Number: 5,914,246
[45] Date of Patent: Jun. 22, 1999

[54] **MULTIPLE DRUG RESISTANCE GENE OF *ASPERGILLUS FUMIGATUS***

[75] Inventors: Robert Brown Peery, Brownsburg; Paul Luther Skatrud; Matthew Barry Tobin, both of Indianapolis, all of Ind.

[73] Assignee: Eli Lilly and Company, Indianapolis, Ind.

[21] Appl. No.: 08/612,734

[22] Filed: Mar. 8, 1996

[51] Int. Cl.$^6$ .............................. C12Q 1/18; C12N 1/15; C12N 15/31; C12N 15/80

[52] U.S. Cl. .................................. 435/32; 435/29; 435/6; 435/69.1; 435/320.1; 435/254.11; 435/254.21; 435/172.3; 536/23.1; 536/24.3

[58] Field of Search .................................... 435/4, 6, 69.1, 435/320.1, 172.3, 254.11, 252.3, 254.21, 29, 32; 536/23.1, 24.3

[56] References Cited

U.S. PATENT DOCUMENTS

| | | | |
|---|---|---|---|
| 4,912,039 | 3/1990 | Riordan | 435/69.1 |
| 5,489,519 | 2/1996 | Deeley et al. | 435/69.1 |
| 5,516,655 | 5/1996 | Peery et al. | 435/69.1 |

OTHER PUBLICATIONS

Price List to 1985/1986 NEN Research Products Catalog, p. 8, Apr. 1985.

Ouellette et al., "The amplified H circle of methotrexate–resistant Leishmania tarentolae contains a novel P–glycoprotein gene", EMBO J: 9(4): 1027–1033, 1990.

Gottesman, M. and Pastan, I., 1993, Annu. Rev. Biochem. 62:385–427.

Pastan, I. and Gottesman, M., 1991, Annu. Rev. Med. 42:277–286.

Raymond, M. et al., 1994, Mol. and Cell. Biol. 14(1):277–286.

Ruetz, S. et al., 1993, Proc. Natl. Acad. Sci. USA 90:11588–11592.

Raymond, M., et al., 1992, Science 256:232–234.

Pastan, I. Gottesman, M., 1987, New Eng. J. of Med. 316(22): 1388–1393.

Parkinson, T. et al., 1995, Antimicrobial Agents and Chemotherapy, 39(8): 1696–1699.

Katzmann, D.J. et al., 1995, Molecular and Cellular Biology, 15(12): 6875–6883.

Balzi, E. et al., 1995, Journal of Bioenergetics and Biomembranes, 27(1): 71–76.

Hirata D., et al., 1994, Current Genetics, 26: 285–294.

Balzi, E. et al., 1994, Biochimica et Biophysica Acta, 1187: 152–162.

Bissinger P.H. et al., 1994, Journal of Biological Chemistry, 296(6): 4180–4186.

Ben–Yaacov, R., et al., 1994, Antimicrobial Agents and Chemotherapy, 38(4): 648–652.

Mitchell–Olds, T., et al., 1995, Heredity, 75: 362–369.

*Primary Examiner*—Jasemine C. Chambers
*Assistant Examiner*—Scott D. Priebe
*Attorney, Agent, or Firm*—Ann I. Craig; Amy E. Hamilton; David E. Boone

[57] ABSTRACT

The invention provides isolated nucleic acid compounds encoding a multiple drug resistance protein of *Aspergillus fumigatus*. Vectors and transformed host cells comprising the multiple drug resistance-encoding DNA of *Aspergillus fumigatus* AfuMDR1 are also provided. The invention further provides assays which utilize these transformed host cells.

16 Claims, 6 Drawing Sheets

SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:
       (A) LENGTH: 4047 base pairs
       (B) TYPE: nucleic acid
       (C) STRANDEDNESS: single
       (D) TOPOLOGY: linear (ii) MOLECULE TYPE: other nucleic acid (ix) FEATURE:
    (A) NAME/KEY: CDS
    (B) LOCATION: 1..4047

(xi) SEQUENCE DESCRIPTION: SEQ ID NO:1:

```
ATG CCT GCG CCT GAA ACC GGC GCC TCC TCT CGG GAG AAG TCC CTC GAG      48
Met Pro Ala Pro Glu Thr Gly Ala Ser Ser Arg Glu Lys Ser Leu Glu
 1               5                  10                  15

GAT TTG CAA GTA GCG ACA TTG GAG AAA GGA CGT TCC ACT TCA TCT TCC      96
Asp Leu Gln Val Ala Thr Leu Glu Lys Gly Arg Ser Thr Ser Ser Ser
             20                  25                  30

GGT GCC GAC AAT GAA AAG CCA CAC GAC CAT CAT TCG TTA TCG GAC ACG     144
Gly Ala Asp Asn Glu Lys Pro His Asp His His Ser Leu Ser Asp Thr
         35                  40                  45

ATC ATG GCG CCT CCA GAT GGC AAG AAA AAG GAT CAC GGG AAA GCT GTC     192
Ile Met Ala Pro Pro Asp Gly Lys Lys Lys Asp His Gly Lys Ala Val
     50                  55                  60

GAC CTG AAC GAT GAT TCT CTC TTT GCC CAT CTC CAG GAG CAC GAG AAA     240
Asp Leu Asn Asp Asp Ser Leu Phe Ala His Leu Gln Glu His Glu Lys
 65                  70                  75                  80

GAG GTA CTC AAG CGA CAG CTT GAT GCA CCG TCT GTG AAA GTC TCT TTC     288
Glu Val Leu Lys Arg Gln Leu Asp Ala Pro Ser Val Lys Val Ser Phe
                 85                  90                  95

TTC ACT TTG TAT CGC TAT GCC TCG AGA AAG GAC ATC CTG ATC ATA CTC     336
Phe Thr Leu Tyr Arg Tyr Ala Ser Arg Lys Asp Ile Leu Ile Ile Leu
            100                 105                 110

GTG AGC GCA ATC TGT GCT ATT GCT GCT GGT GCC GCT CTT CCC TTG TTC     384
Val Ser Ala Ile Cys Ala Ile Ala Ala Gly Ala Ala Leu Pro Leu Phe
        115                 120                 125

ACA ATT CTC TTC GGT TCA CTA GCC TCA GCG TTC CAG GGC ATA TCT CTG     432
Thr Ile Leu Phe Gly Ser Leu Ala Ser Ala Phe Gln Gly Ile Ser Leu
130                 135                 140

GGT ACT ATG CCC TAT CAT GAG TTC TAT CAC AAA CTG ACT AAG AAT GTG     480
Gly Thr Met Pro Tyr His Glu Phe Tyr His Lys Leu Thr Lys Asn Val
145                 150                 155                 160

CTT TAC TTT GTG TAT CTC GGT ATT GCC GAG TTT GTC ACA GTC TAT GTC     528
Leu Tyr Phe Val Tyr Leu Gly Ile Ala Glu Phe Val Thr Val Tyr Val
                165                 170                 175

AGC ACC GTG GGT TTC ATT TAT ACT GGC GAA CAT CTC ACA CAG AAG ATC     576
Ser Thr Val Gly Phe Ile Tyr Thr Gly Glu His Leu Thr Gln Lys Ile
            180                 185                 190

CGT GAA AAT TAT CTT GAG GCT ATC CTG AGG CAG AAT ATG GCT TAC TTC     624
Arg Glu Asn Tyr Leu Glu Ala Ile Leu Arg Gln Asn Met Ala Tyr Phe
        195                 200                 205

GAC AAG TTG GGC GCC GGT GAA GTT ACC ACG CGT ATC ACT GCT GAT ACC     672
Asp Lys Leu Gly Ala Gly Glu Val Thr Thr Arg Ile Thr Ala Asp Thr
210                 215                 220

AAC CTG ATC CAG GAC GCC ATC TCT GAG AAA GTT GGT CTC ACT TTG ACC     720
Asn Leu Ile Gln Asp Ala Ile Ser Glu Lys Val Gly Leu Thr Leu Thr
225                 230                 235                 240

GCA TTC GCC ACA TTT GTA ACC GCA TTT ATT GTC GCC TAC GTC AAG TAT     768
Ala Phe Ala Thr Phe Val Thr Ala Phe Ile Val Ala Tyr Val Lys Tyr
                245                 250                 255

TGG AAG TTG GCT CTG ATC TGT ACC TCA ACT ATC GTC GCG CTG GTC ATG     816
Trp Lys Leu Ala Leu Ile Cys Thr Ser Thr Ile Val Ala Leu Val Met
            260                 265                 270

GTT ATG GGA GGT GGG TCG AGG TTT ATT GTG AAG TAC AGC AAG AAA TCT     864
Val Met Gly Gly Gly Ser Arg Phe Ile Val Lys Tyr Ser Lys Lys Ser
        275                 280                 285
```

```
ATT GAA AGT TAT GGT GCT GGT GGA ACT GTC GCG GAA GAA GTC ATC AGC      912
Ile Glu Ser Tyr Gly Ala Gly Gly Thr Val Ala Glu Glu Val Ile Ser
    290                 295                 300

TCC ATT CGG AAT GCT ACC GCT TTC GGC ACT CAG GAT AAG CTC GCC AAG      960
Ser Ile Arg Asn Ala Thr Ala Phe Gly Thr Gln Asp Lys Leu Ala Lys
305                 310                 315                 320

CAA TAC GAA ACC CAT CTG GCT GAG GCT GAA AAA TGG GGC GTC AAA CAA     1008
Gln Tyr Glu Thr His Leu Ala Glu Ala Glu Lys Trp Gly Val Lys Gln
                325                 330                 335

CAG GTC ATC CTT GGT ATG ATG ATT GGT GGT ATG TTC GGT ATC ATG TTC     1056
Gln Val Ile Leu Gly Met Met Ile Gly Gly Met Phe Gly Ile Met Phe
        340                 345                 350

TCG AAC TAT GGT CTC GGT TTC TGG ATG GGA TCT CGC TTC GTT GTC GGT     1104
Ser Asn Tyr Gly Leu Gly Phe Trp Met Gly Ser Arg Phe Val Val Gly
                355                 360                 365

AAA GAA GTC AAC GTG GGC CAA GTT CTG ACA GTT TTG ATG TCT ATC CTG     1152
Lys Glu Val Asn Val Gly Gln Val Leu Thr Val Leu Met Ser Ile Leu
370                 375                 380

ATC GGT TCG TTC AGT TTG GGC AAC GTC GCC CCC AAT GGT CAG GCC TTT     1200
Ile Gly Ser Phe Ser Leu Gly Asn Val Ala Pro Asn Gly Gln Ala Phe
385                 390                 395                 400

ACG AAT GGT GTT GCT GCG GCC GCG AAG ATT TAC AGC ACG ATT GAC CGC     1248
Thr Asn Gly Val Ala Ala Ala Ala Lys Ile Tyr Ser Thr Ile Asp Arg
                405                 410                 415

AGA TCG CCA CTG GAC CCC TAT TCT GAC GAA GGG AAG GTA CTC GAC CAT     1296
Arg Ser Pro Leu Asp Pro Tyr Ser Asp Glu Gly Lys Val Leu Asp His
        420                 425                 430

TTT GAA GGA AAT ATC GAA TTT CGC AAT GTC AAA CAC ATC TAC CCT TCA     1344
Phe Glu Gly Asn Ile Glu Phe Arg Asn Val Lys His Ile Tyr Pro Ser
                435                 440                 445

AGA CCC GAA GTT ACA GTC ATG GAA GAT GTC TCT TTA TCG ATG CCC GCC     1392
Arg Pro Glu Val Thr Val Met Glu Asp Val Ser Leu Ser Met Pro Ala
450                 455                 460

GGA AAG ACT ACC GCA TTG GTG GGC CCA TCT GGC TCT GGA AAG AGT ACT     1440
Gly Lys Thr Thr Ala Leu Val Gly Pro Ser Gly Ser Gly Lys Ser Thr
465                 470                 475                 480

GTT GTC GGC TTG GTG GAG CGC TTT TAC CTT CCA GTA GGA GGC CAG GTA     1488
Val Val Gly Leu Val Glu Arg Phe Tyr Leu Pro Val Gly Gly Gln Val
                485                 490                 495

TTG CTG GAC GGC CAT GAT ATC CAA ACC CTC AAC CTC CGT TGG CTG CGA     1536
Leu Leu Asp Gly His Asp Ile Gln Thr Leu Asn Leu Arg Trp Leu Arg
        500                 505                 510

CAG CAG ATC TCT CTT GTC AGC CAG GAA CCT GTT CTT TTC AGC ACC ACG     1584
Gln Gln Ile Ser Leu Val Ser Gln Glu Pro Val Leu Phe Ser Thr Thr
            515                 520                 525

ATC TTT AGA AAC ATC GAA CAT GGC TTG ATT GGC ACC AAA TTC GAG CAT     1632
Ile Phe Arg Asn Ile Glu His Gly Leu Ile Gly Thr Lys Phe Glu His
530                 535                 540

GAG TCG AAG GAC AAG ATT AGA GAG CTC GTT GAG AAT GCG GCC AGA ATG     1680
Glu Ser Lys Asp Lys Ile Arg Glu Leu Val Glu Asn Ala Ala Arg Met
545                 550                 555                 560

GCC AAT GCT CAT GAT TTT ATT ATG GCT CTG CCT GAA GGT TAC GAT ACG     1728
Ala Asn Ala His Asp Phe Ile Met Ala Leu Pro Glu Gly Tyr Asp Thr
                565                 570                 575

AAT GTG GGT CAG CGT GGT TTC TTA CTT TCA GGA GGT CAG AAG CAA CGT     1776
Asn Val Gly Gln Arg Gly Phe Leu Leu Ser Gly Gly Gln Lys Gln Arg
        580                 585                 590

ATT GCC ATT GCT CGT GCC ATT GTC AGT GAC CCC AAG ATT CTG TTG CTT     1824
Ile Ala Ile Ala Arg Ala Ile Val Ser Asp Pro Lys Ile Leu Leu Leu
            595                 600                 605
```

```
GAT GAA GCT ACA TCA GCT TTG GAT ACC AAG TCC GAG GGC GTC GTC CAA    1872
Asp Glu Ala Thr Ser Ala Leu Asp Thr Lys Ser Glu Gly Val Val Gln
        610                 615                 620

GCC GCT CTT GAT AAA GCT GCC GAG GGT AGA ACT ACC ATT GTC ATT GCT    1920
Ala Ala Leu Asp Lys Ala Ala Glu Gly Arg Thr Thr Ile Val Ile Ala
625                 630                 635                 640

CAC CGT TTG TCA ACA ATC AAA ACA GCC CAC AAC ATT GTT GCC ATG GTC    1968
His Arg Leu Ser Thr Ile Lys Thr Ala His Asn Ile Val Ala Met Val
                645                 650                 655

GGC GGA AAG ATT GCC GAA CAG GGA ACA CAT GAC GAA TTG GTC GAT CGC    2016
Gly Gly Lys Ile Ala Glu Gln Gly Thr His Asp Glu Leu Val Asp Arg
            660                 665                 670

AAA GGC ACG TAC TAT AAA CTT GTG GAG GCG CAA CGT ATC AAC GAG GAG    2064
Lys Gly Thr Tyr Tyr Lys Leu Val Glu Ala Gln Arg Ile Asn Glu Glu
        675                 680                 685

AAG GAA GCA GAA GCT CTG GAA GCC GAC GCC GAC ATG GAC GCC GAT GAT    2112
Lys Glu Ala Glu Ala Leu Glu Ala Asp Ala Asp Met Asp Ala Asp Asp
690                 695                 700

TTT GGT CAA GAA GGG GTT ACT CGC ATC AAG ACT GCA GTT AGC AGC TCG    2160
Phe Gly Gln Glu Gly Val Thr Arg Ile Lys Thr Ala Val Ser Ser Ser
705                 710                 715                 720

AAT TCT CTC GAT GCT GTA GAT GAG AAG GCG CGC TTG GAG ATG AAG CGA    2208
Asn Ser Leu Asp Ala Val Asp Glu Lys Ala Arg Leu Glu Met Lys Arg
                725                 730                 735

ACC GGA ACG CAA AAA TCG GTT TCG AGT GCC GTT CTA TCT AAG AAA GTC    2256
Thr Gly Thr Gln Lys Ser Val Ser Ser Ala Val Leu Ser Lys Lys Val
            740                 745                 750

CCC GAG CAG TTC GAG AAG TAT TCA CTC TGG ACC CTC GTC AAG TTC ATC    2304
Pro Glu Gln Phe Glu Lys Tyr Ser Leu Trp Thr Leu Val Lys Phe Ile
        755                 760                 765

GGT GCA TTT AAC CGC CCT GAG CTT GGT TAC ATG CTC ATT GGC TTG ACT    2352
Gly Ala Phe Asn Arg Pro Glu Leu Gly Tyr Met Leu Ile Gly Leu Thr
770                 775                 780

TTC TCG TTC CTT GCC GGT GGT GGT CAA CCT ACC CAG GCT TTT CTG TAC    2400
Phe Ser Phe Leu Ala Gly Gly Gly Gln Pro Thr Gln Ala Phe Leu Tyr
785                 790                 795                 800

GCC AAG GCA ATT AGC ACG CTC TCG TTA CCC GAA TCA ATG TTT CAC AAA    2448
Ala Lys Ala Ile Ser Thr Leu Ser Leu Pro Glu Ser Met Phe His Lys
                805                 810                 815

CTC AGG CAT GAC GCG AAT TTC TGG TCC TTG ATG TTC TTC GTG GTT GGA    2496
Leu Arg His Asp Ala Asn Phe Trp Ser Leu Met Phe Phe Val Val Gly
            820                 825                 830

ATT GCT CAA TTT ATC AGC CTG TCT ATC AAT GGT ACA GCA TTT GCT ATT    2544
Ile Ala Gln Phe Ile Ser Leu Ser Ile Asn Gly Thr Ala Phe Ala Ile
        835                 840                 845

TGT TCG GAG AGA CTC ATT CGC CGA GCT AGA AGT CAA GCG TTT AGA TCG    2592
Cys Ser Glu Arg Leu Ile Arg Arg Ala Arg Ser Gln Ala Phe Arg Ser
850                 855                 860

ATT CTT CGT CAG GAC ATC TCA TTT TTC GAC AGG GAA GAG AAC AGC ACC    2640
Ile Leu Arg Gln Asp Ile Ser Phe Phe Asp Arg Glu Glu Asn Ser Thr
865                 870                 875                 880

GGT GCC TTG ACG TCC TTC TTA TCA ACA GAG ACG AAG AAT CTG TCG GGC    2688
Gly Ala Leu Thr Ser Phe Leu Ser Thr Glu Thr Lys Asn Leu Ser Gly
                885                 890                 895

GTT AGC GGA GTG ACT CTC GGC ACA ATC ATC ATG ACT AGC ACT ACG CTT    2736
Val Ser Gly Val Thr Leu Gly Thr Ile Ile Met Thr Ser Thr Thr Leu
            900                 905                 910

GGG GCG GCG ATG ATC ATT GCA TTG GCG ATC GGA TGG AAG CTG GCT CTG    2784
Gly Ala Ala Met Ile Ile Ala Leu Ala Ile Gly Trp Lys Leu Ala Leu
        915                 920                 925
```

-continued

```
GTT TGC ATT TCT GTC GTT CCA ATC CTT CTG GCA TGC GGC TTC CTC AGA        2832
Val Cys Ile Ser Val Val Pro Ile Leu Leu Ala Cys Gly Phe Leu Arg
    930                 935                 940

TTC TAC ATG CTT GCT CAA TTC CAG CAA CGA TCG AAG TCT GCC TAC GAA        2880
Phe Tyr Met Leu Ala Gln Phe Gln Gln Arg Ser Lys Ser Ala Tyr Glu
945                 950                 955                 960

GGG TCT GCG AGC TAT GCT TGC GAA GCC ACG TCA GCG ATC CGC ACT GTA        2928
Gly Ser Ala Ser Tyr Ala Cys Glu Ala Thr Ser Ala Ile Arg Thr Val
                965                 970                 975

GCA TCA CTC ACT CGC GAA CAA GAT GTC TGG GGC GTT TAC CAC GAC CAG        2976
Ala Ser Leu Thr Arg Glu Gln Asp Val Trp Gly Val Tyr His Asp Gln
            980                 985                 990

CTA CAA AAA CAG GGA CGG AAG AGT TTG ATC TCA GTG CTG AGA TCC TCC        3024
Leu Gln Lys Gln Gly Arg Lys Ser Leu Ile Ser Val Leu Arg Ser Ser
        995                 1000                1005

CTG CTG TAT GCC TCG TCG CAG GCA TTG GTG TTT TTC TGC GTC GCT TTG        3072
Leu Leu Tyr Ala Ser Ser Gln Ala Leu Val Phe Phe Cys Val Ala Leu
    1010                1015                1020

GGC TTC TGG TAT GGT GGT ACA CTT CTA GGC CAT CAT GAG TAC AGC ATC        3120
Gly Phe Trp Tyr Gly Gly Thr Leu Leu Gly His His Glu Tyr Ser Ile
1025                1030                1035                1040

TTC CGC TTC TTC GTC TGC TTT TCT GAG ATT CTT TTT GGT GCG CAA TCA        3168
Phe Arg Phe Phe Val Cys Phe Ser Glu Ile Leu Phe Gly Ala Gln Ser
                1045                1050                1055

GCC GGA ACT GTC TTC TCT TTT GCC CCG GAC ATG GGT AAG GCA AAG AAT        3216
Ala Gly Thr Val Phe Ser Phe Ala Pro Asp Met Gly Lys Ala Lys Asn
            1060                1065                1070

GCC GCT GCT CAA TTC AAG AAA CTC TTC GAC AGC AAG CCA ACC ATT GAC        3264
Ala Ala Ala Gln Phe Lys Lys Leu Phe Asp Ser Lys Pro Thr Ile Asp
        1075                1080                1085

ATC TGG TCG GAT GAG GGC GAG AAG TTG GAG TCT ATG GAA GGC GAA ATC        3312
Ile Trp Ser Asp Glu Gly Glu Lys Leu Glu Ser Met Glu Gly Glu Ile
    1090                1095                1100

GAA TTC CGG GAC GTC CAC TTT AGG TAC CCA ACG CGG CCG GAG CAG CCT        3360
Glu Phe Arg Asp Val His Phe Arg Tyr Pro Thr Arg Pro Glu Gln Pro
1105                1110                1115                1120

GTT CTT CGA GGA CTG AAT TTG AGC GTG AAG CCT GGA CAA TAC ATT GCC        3408
Val Leu Arg Gly Leu Asn Leu Ser Val Lys Pro Gly Gln Tyr Ile Ala
                1125                1130                1135

CTT GTT GGA CCC AGT GGA TGC GGT AAG AGC ACT ACG ATT GCT CTG CTT        3456
Leu Val Gly Pro Ser Gly Cys Gly Lys Ser Thr Thr Ile Ala Leu Leu
            1140                1145                1150

GAG CGA TTT TAT GAC GCA CTT GCT GGA GGG GTC TTC GTT GAC GGA AAG        3504
Glu Arg Phe Tyr Asp Ala Leu Ala Gly Gly Val Phe Val Asp Gly Lys
        1155                1160                1165

GAC ATT ACC AAA CTC AAT GTC AAC TCA TAC CGC AGT TTC CTC TCC CTT        3552
Asp Ile Thr Lys Leu Asn Val Asn Ser Tyr Arg Ser Phe Leu Ser Leu
    1170                1175                1180

GTC AGC CAA GAA CCT ACT CTG TAT CAG GGT ACC ATC AAG GAA AAT ATC        3600
Val Ser Gln Glu Pro Thr Leu Tyr Gln Gly Thr Ile Lys Glu Asn Ile
1185                1190                1195                1200

CTG CTT GGA GTC GAT AAG GAT GAC GTT TCG GAG GAG ACT TTG ATT AAG        3648
Leu Leu Gly Val Asp Lys Asp Asp Val Ser Glu Glu Thr Leu Ile Lys
                1205                1210                1215

GTC TGC AAA GAT GCC AAC ATC TAT GAT TTC GTT ATG TCA CTC CCT GAG        3696
Val Cys Lys Asp Ala Asn Ile Tyr Asp Phe Val Met Ser Leu Pro Glu
            1220                1225                1230

GGA TTT GAC ACC GTC GTT GGC AGC AAG GGA GGC ATG TTG TCT GGT GGA        3744
Gly Phe Asp Thr Val Val Gly Ser Lys Gly Gly Met Leu Ser Gly Gly
        1235                1240                1245
```

```
CAA AAA CAG CGT GTC GCC ATT GCT CGT GCC CTC CTG CGT GAC CCC AAG          3792
Gln Lys Gln Arg Val Ala Ile Ala Arg Ala Leu Leu Arg Asp Pro Lys
1250                1255                1260

GTC CTT CTT CTG GAT GAA GCC ACA TCT GCT CTT GAC TCC GAA TCT GAG          3840
Val Leu Leu Leu Asp Glu Ala Thr Ser Ala Leu Asp Ser Glu Ser Glu
1265                1270                1275                1280

AAA GTC GTA CAA GCT GCG CTG GAT GCT GCT GCC CGC GGG CGG ACA ACG          3888
Lys Val Val Gln Ala Ala Leu Asp Ala Ala Ala Arg Gly Arg Thr Thr
                    1285                1290                1295

ATT GCT GTT GCC CAC CGG CTG AGC ACC ATT CAA AAC GCT GAT ATA ATT          3936
Ile Ala Val Ala His Arg Leu Ser Thr Ile Gln Asn Ala Asp Ile Ile
                1300                1305                1310

TAC GTG TTC GAC CAA GGC AAG ATC GTC GAA AGT GGA ACG CAC CAC GAG          3984
Tyr Val Phe Asp Gln Gly Lys Ile Val Glu Ser Gly Thr His His Glu
            1315                1320                1325

TTG ATT CGA AAC AAG GGC CGG TAT TAC GAG CTG GTC AAT CTG CAG AGT          4032
Leu Ile Arg Asn Lys Gly Arg Tyr Tyr Glu Leu Val Asn Leu Gln Ser
        1330                1335                1340

CTC GGA AAG ACT CAT                                                       4047
Leu Gly Lys Thr His
1345
```

(2) INFORMATION FOR SEQ ID NO:2:

(i) SEQUENCE CHARACTERISTICS:
        (A) LENGTH: 1349 amino acids
        (B) TYPE: amino acid
        (D) TOPOLOGY: linear (ii) MOLECULE TYPE: protein (xi) SEQUENCE DESCRIPTION: SEQ ID NO:2:

```
Met Pro Ala Pro Glu Thr Gly Ala Ser Ser Arg Glu Lys Ser Leu Glu
1               5                   10                  15

Asp Leu Gln Val Ala Thr Leu Glu Lys Gly Arg Ser Thr Ser Ser Ser
            20                  25                  30

Gly Ala Asp Asn Glu Lys Pro His Asp His His Ser Leu Ser Asp Thr
        35                  40                  45

Ile Met Ala Pro Pro Asp Gly Lys Lys Lys Asp His Gly Lys Ala Val
50                  55                  60

Asp Leu Asn Asp Asp Ser Leu Phe Ala His Leu Gln Glu His Glu Lys
65                  70                  75                  80

Glu Val Leu Lys Arg Gln Leu Asp Ala Pro Ser Val Lys Val Ser Phe
                85                  90                  95

Phe Thr Leu Tyr Arg Tyr Ala Ser Arg Lys Asp Ile Leu Ile Ile Leu
            100                 105                 110

Val Ser Ala Ile Cys Ala Ile Ala Ala Gly Ala Ala Leu Pro Leu Phe
        115                 120                 125

Thr Ile Leu Phe Gly Ser Leu Ala Ser Ala Phe Gln Gly Ile Ser Leu
130                 135                 140

Gly Thr Met Pro Tyr His Glu Phe Tyr His Lys Leu Thr Lys Asn Val
145                 150                 155                 160

Leu Tyr Phe Val Tyr Leu Gly Ile Ala Glu Phe Val Thr Val Tyr Val
                165                 170                 175

Ser Thr Val Gly Phe Ile Tyr Thr Gly Glu His Leu Thr Gln Lys Ile
            180                 185                 190

Arg Glu Asn Tyr Leu Glu Ala Ile Leu Arg Gln Asn Met Ala Tyr Phe
        195                 200                 205
```

```
Asp Lys Leu Gly Ala Gly Glu Val Thr Thr Arg Ile Thr Ala Asp Thr
210                 215                 220

Asn Leu Ile Gln Asp Ala Ile Ser Glu Lys Val Gly Leu Thr Leu Thr
225                 230                 235                 240

Ala Phe Ala Thr Phe Val Thr Ala Phe Ile Val Ala Tyr Val Lys Tyr
                245                 250                 255

Trp Lys Leu Ala Leu Ile Cys Thr Ser Thr Ile Val Ala Leu Val Met
                260                 265                 270

Val Met Gly Gly Gly Ser Arg Phe Ile Val Lys Tyr Ser Lys Lys Ser
                275                 280                 285

Ile Glu Ser Tyr Gly Ala Gly Gly Thr Val Ala Glu Glu Val Ile Ser
290                 295                 300

Ser Ile Arg Asn Ala Thr Ala Phe Gly Thr Gln Asp Lys Leu Ala Lys
305                 310                 315                 320

Gln Tyr Glu Thr His Leu Ala Glu Ala Glu Lys Trp Gly Val Lys Gln
                325                 330                 335

Gln Val Ile Leu Gly Met Met Ile Gly Met Phe Gly Ile Met Phe
                340                 345                 350

Ser Asn Tyr Gly Leu Gly Phe Trp Met Gly Ser Arg Phe Val Val Gly
                355                 360                 365

Lys Glu Val Asn Val Gly Gln Val Leu Thr Val Leu Met Ser Ile Leu
370                 375                 380

Ile Gly Ser Phe Ser Leu Gly Asn Val Ala Pro Asn Gly Gln Ala Phe
385                 390                 395                 400

Thr Asn Gly Val Ala Ala Ala Lys Ile Tyr Ser Thr Ile Asp Arg
                405                 410                 415

Arg Ser Pro Leu Asp Pro Tyr Ser Asp Glu Gly Lys Val Leu Asp His
                420                 425                 430

Phe Glu Gly Asn Ile Glu Phe Arg Asn Val Lys His Ile Tyr Pro Ser
                435                 440                 445

Arg Pro Glu Val Thr Val Met Glu Asp Val Ser Leu Ser Met Pro Ala
450                 455                 460

Gly Lys Thr Thr Ala Leu Val Gly Pro Ser Gly Ser Gly Lys Ser Thr
465                 470                 475                 480

Val Val Gly Leu Val Glu Arg Phe Tyr Leu Pro Val Gly Gly Gln Val
                485                 490                 495

Leu Leu Asp Gly His Asp Ile Gln Thr Leu Asn Leu Arg Trp Leu Arg
                500                 505                 510

Gln Gln Ile Ser Leu Val Ser Gln Glu Pro Val Leu Phe Ser Thr Thr
                515                 520                 525

Ile Phe Arg Asn Ile Glu His Gly Leu Ile Gly Thr Lys Phe Glu His
530                 535                 540

Glu Ser Lys Asp Lys Ile Arg Glu Leu Val Glu Asn Ala Ala Arg Met
545                 550                 555                 560

Ala Asn Ala His Asp Phe Ile Met Ala Leu Pro Glu Gly Tyr Asp Thr
                565                 570                 575

Asn Val Gly Gln Arg Gly Phe Leu Leu Ser Gly Gly Gln Lys Gln Arg
                580                 585                 590

Ile Ala Ile Ala Arg Ala Ile Val Ser Asp Pro Lys Ile Leu Leu Leu
595                 600                 605

Asp Glu Ala Thr Ser Ala Leu Asp Thr Lys Ser Glu Gly Val Val Gln
                610                 615                 620

Ala Ala Leu Asp Lys Ala Ala Glu Gly Arg Thr Thr Ile Val Ile Ala
625                 630                 635                 640
```

```
His Arg Leu Ser Thr Ile Lys Thr Ala His Asn Ile Val Ala Met Val
                645                 650                 655
Gly Gly Lys Ile Ala Glu Gln Gly Thr His Asp Glu Leu Val Asp Arg
            660                 665                 670
Lys Gly Thr Tyr Tyr Lys Leu Val Glu Ala Gln Arg Ile Asn Glu Glu
            675                 680                 685
Lys Glu Ala Glu Ala Leu Glu Ala Asp Ala Asp Met Asp Ala Asp Asp
690                 695                 700
Phe Gly Gln Glu Gly Val Thr Arg Ile Lys Thr Ala Val Ser Ser Ser
705                 710                 715                 720
Asn Ser Leu Asp Ala Val Asp Glu Lys Ala Arg Leu Glu Met Lys Arg
                725                 730                 735
Thr Gly Thr Gln Lys Ser Val Ser Ala Val Leu Ser Lys Lys Val
            740                 745                 750
Pro Glu Gln Phe Glu Lys Tyr Ser Leu Trp Thr Leu Val Lys Phe Ile
                755                 760                 765
Gly Ala Phe Asn Arg Pro Glu Leu Gly Tyr Met Leu Ile Gly Leu Thr
770                 775                 780
Phe Ser Phe Leu Ala Gly Gly Gln Pro Thr Gln Ala Phe Leu Tyr
785                 790                 795                 800
Ala Lys Ala Ile Ser Thr Leu Ser Leu Pro Glu Ser Met Phe His Lys
                805                 810                 815
Leu Arg His Asp Ala Asn Phe Trp Ser Leu Met Phe Val Val Gly
                820                 825                 830
Ile Ala Gln Phe Ile Ser Leu Ser Ile Asn Gly Thr Ala Phe Ala Ile
                835                 840                 845
Cys Ser Glu Arg Leu Ile Arg Arg Ala Arg Ser Gln Ala Phe Arg Ser
850                 855                 860
Ile Leu Arg Gln Asp Ile Ser Phe Phe Asp Arg Glu Glu Asn Ser Thr
865                 870                 875                 880
Gly Ala Leu Thr Ser Phe Leu Ser Thr Glu Thr Lys Asn Leu Ser Gly
                885                 890                 895
Val Ser Gly Val Thr Leu Gly Thr Ile Ile Met Thr Ser Thr Thr Leu
            900                 905                 910
Gly Ala Ala Met Ile Ile Ala Leu Ala Ile Gly Trp Lys Leu Ala Leu
                915                 920                 925
Val Cys Ile Ser Val Val Pro Ile Leu Leu Ala Cys Gly Phe Leu Arg
                930                 935                 940
Phe Tyr Met Leu Ala Gln Phe Gln Gln Arg Ser Lys Ser Ala Tyr Glu
945                 950                 955                 960
Gly Ser Ala Ser Tyr Ala Cys Glu Ala Thr Ser Ala Ile Arg Thr Val
                965                 970                 975
Ala Ser Leu Thr Arg Glu Gln Asp Val Trp Gly Val Tyr His Asp Gln
            980                 985                 990
Leu Gln Lys Gln Gly Arg Lys Ser Leu Ile Ser Val Leu Arg Ser Ser
                995                 1000                1005
Leu Leu Tyr Ala Ser Ser Gln Ala Leu Val Phe Phe Cys Val Ala Leu
            1010                1015                1020
Gly Phe Trp Tyr Gly Gly Thr Leu Leu Gly His His Glu Tyr Ser Ile
1025                1030                1035                1040
Phe Arg Phe Phe Val Cys Phe Ser Glu Ile Leu Phe Gly Ala Gln Ser
                1045                1050                1055
```

```
Ala Gly Thr Val Phe Ser Phe Ala Pro Asp Met Gly Lys Ala Lys Asn
            1060                1065                1070

Ala Ala Ala Gln Phe Lys Lys Leu Phe Asp Ser Lys Pro Thr Ile Asp
        1075                1080                1085

Ile Trp Ser Asp Glu Gly Glu Lys Leu Glu Ser Met Glu Gly Glu Ile
    1090                1095                1100

Glu Phe Arg Asp Val His Phe Arg Tyr Pro Thr Arg Pro Glu Gln Pro
1105                1110                1115                1120

Val Leu Arg Gly Leu Asn Leu Ser Val Lys Pro Gly Gln Tyr Ile Ala
            1125                1130                1135

Leu Val Gly Pro Ser Gly Cys Gly Lys Ser Thr Thr Ile Ala Leu Leu
            1140                1145                1150

Glu Arg Phe Tyr Asp Ala Leu Ala Gly Gly Val Phe Val Asp Gly Lys
        1155                1160                1165

Asp Ile Thr Lys Leu Asn Val Asn Ser Tyr Arg Ser Phe Leu Ser Leu
    1170                1175                1180

Val Ser Gln Glu Pro Thr Leu Tyr Gln Gly Thr Ile Lys Glu Asn Ile
1185                1190                1195                1200

Leu Leu Gly Val Asp Lys Asp Val Ser Glu Glu Thr Leu Ile Lys
            1205                1210                1215

Val Cys Lys Asp Ala Asn Ile Tyr Asp Phe Val Met Ser Leu Pro Glu
        1220                1225                1230

Gly Phe Asp Thr Val Val Gly Ser Lys Gly Gly Met Leu Ser Gly Gly
        1235                1240                1245

Gln Lys Gln Arg Val Ala Ile Ala Arg Ala Leu Leu Arg Asp Pro Lys
        1250                1255                1260

Val Leu Leu Leu Asp Glu Ala Thr Ser Ala Leu Asp Ser Glu Ser Glu
1265                1270                1275                1280

Lys Val Val Gln Ala Ala Leu Asp Ala Ala Ala Arg Gly Arg Thr Thr
            1285                1290                1295

Ile Ala Val Ala His Arg Leu Ser Thr Ile Gln Asn Ala Asp Ile Ile
            1300                1305                1310

Tyr Val Phe Asp Gln Gly Lys Ile Val Glu Ser Gly Thr His His Glu
        1315                1320                1325

Leu Ile Arg Asn Lys Gly Arg Tyr Tyr Glu Leu Val Asn Leu Gln Ser
        1330                1335                1340

Leu Gly Lys Thr His
1345

(2) INFORMATION FOR SEQ ID NO:3:

(i) SEQUENCE CHARACTERISTICS:
        (A) LENGTH: 4800 base pairs
        (B) TYPE: nucleic acid
        (C) STRANDEDNESS: double
        (D) TOPOLOGY: linear (ii) MOLECULE TYPE: other nucleic acid (xi) SEQUENCE DESCRIPTION: SEQ ID NO:3:

TATAGAAGTG TCCTTTCTAC AAGGGGAGT AAGACAGGCC CTTACGACAG CATCTCAGAC      60

TACTCTCTTC TACAATCCTC CTTGATTCGC TCGAGTTCCG GAAACCAGAT TGTCCGCCAG    120

TTAACCAACT CATGGAGTAG TGCGATTCTG ATTGTGTGAG GATTCCTCAA TCTGTGACAT    180

CTTTATCTGA GAGAATCAGT TTTGGCATAC CCTCAACCGC AACATGCCTG CGCCTGAAAC    240

CGGCGCCTCC TCTCGGGAGA AGTCCCTCGA GGATTTGCAA GTAGCGACAT TGGAGAAAGG    300
```

```
ACGTTCCACT TCATCTTCCG GTGCCGACAA TGAAAAGCCA CACGACCATC ATTCGTTATC    360

GGACACGATC ATGGCGCCTC CAGATGGCAA GAAAAAGGAT CACGGGAAAG CTGTCGACCT    420

GAACGATGAT TCTCTCTTTG CCCATCTCCA GGAGCACGAG AAAGAGGTAC TCAAGCGACA    480

GCTTGATGCA CCGTCTGTGA AAGTCTCTTT CTTCACTTTG TATCGCTATG CCTCGAGAAA    540

GGACATCCTG ATCATACTCG TGAGCGCAAT CTGTGCTATT GCTGCTGGTG CCGCTCTTCC    600

CTTGTTCACA GTATGTATGA CCTGCCTAGC AATGTCCCTA TTTGTCAGTC ATTAGAACAA    660

AGAGCTTTTG CAGCTGACGT TTGATCTACT AGATTCTCTT CGGTTCACTA GCCTCAGCGT    720

TCCAGGGCAT ATCTCTGGGT ACTATGCCCT ATCATGAGTT CTATCACAAA CTGACTAAGA    780

ATGTGCTTTA CTTTGTGTAT CTCGGTATTG CCGAGTTTGT CACAGTCTAT GTCAGCACCG    840

TGGGTTTCAT TTATACTGGC GAACATCTCA CACAGAAGAT CCGTGAAAAT TATCTTGAGG    900

CTATCCTGAG GCAGAATATG GCTTACTTCG ACAAGTTGGG CGCCGGTGAA GTTACCACGC    960

GTATCACTGC TGATACCAAC CTGATCCAGG ACGCCATCTC TGAGAAAGTT GGTCTCACTT   1020

TGACCGCATT CGCCACATTT GTAACCGCAT TTATTGTCGC CTACGTCAAG TATTGGAAGT   1080

TGGCTCTGAT CTGTACCTCA ACTATCGTCG CGCTGGTCAT GGTTATGGGA GGTGGGTCGA   1140

GGTTTATTGT GAAGTACAGC AAGAAATCTA TTGAAAGTTA TGGTGCTGGT GGAACTGTCG   1200

CGGAAGAAGT CATCAGCTCC ATTCGGAATG CTACCGCTTT CGGCACTCAG GATAAGCTCG   1260

CCAAGCAATA CGAAACCCAT CTGGCTGAGG CTGAAAAATG GGGCGTCAAA CAACAGGTCA   1320

TCCTTGGTAT GATGATTGGT GGTATGTTCG GTATCATGTT CTCGAACTAT GGTCTCGGTT   1380

TCTGGATGGG ATCTCGCTTC GTTGTCGGTA AGAAGTCAA CGTGGGCCAA GTTCTGACAG   1440

TTTTGATGTC TATCCTGATC GGTTCGTTCA GTTTGGGCAA CGTCGCCCCC AATGGTCAGG   1500

CCTTTACGAA TGGTGTTGCT GCGGCCGCGA AGATTTACAG CACGATTGAC CGCAGATCGC   1560

CACTGGACCC CTATTCTGAC GAAGGGAAGG TACTCGACCA TTTTGAAGGA AATATCGAAT   1620

TTCGCAATGT CAAACACATC TACCCTTCAA GACCCGAAGT TACAGTCATG GAAGATGTCT   1680

CTTTATCGAT GCCCGCCGGA AAGACTACCG CATTGGTGGG CCCATCTGGC TCTGGAAAGA   1740

GTACTGTTGT CGGCTTGGTG GAGCGCTTTT ACCTTCCAGT AGGAGGCCAG GTATTGCTGG   1800

ACGGCCATGA TATCCAAACC CTCAACCTCC GTTGGCTGCG ACAGCAGATC TCTCTTGTCA   1860

GCCAGGAACC TGTTCTTTTC AGCACCACGA TCTTTAGAAA CATCGAACAT GGCTTGATTG   1920

GCACCAAATT CGAGCATGAG TCGAAGGACA AGATTAGAGA GCTCGTTGAG AATGCGGCCA   1980

GAATGGCCAA TGCTCATGAT TTTATTATGG CTCTGCCTGA AGGTTACGAT ACGAATGTGG   2040

GTCAGCGTGG TTTCTTACTT TCAGGAGGTC AGAAGCAACG TATTGCCATT GCTCGTGCCA   2100

TTGTCAGTGA CCCCAAGATT CTGTTGCTTG ATGAAGCTAC ATCAGCTTTG GATACCAAGT   2160

CCGAGGGCGT CGTCCAAGCC GCTCTTGATA AAGCTGCCGA GGGTAGAACT ACCATTGTCA   2220

TTGCTCACCG TTTGTCAACA ATCAAAACAG CCCACAACAT TGTTGCCATG GTCGGCGGAA   2280

AGATTGCCGA ACAGGGAACA CATGACGAAT TGGTCGATCG CAAAGGCACG TACTATAAAC   2340

TTGTGGAGGC GCAACGTATC AACGAGGAGA AGGAAGCAGA AGCTCTGGAA GCCGACGCCG   2400

ACATGGACGC CGATGATTTT GGTCAAGAAG GGGTTACTCG CATCAAGACT GCAGTTAGCA   2460

GCTCGAATTC TCTCGATGCT GTAGATGAGA AGGCGCGCTT GGAGATGAAG CGAACCGGAA   2520

CGCAAAAATC GGTTTCGAGT GCCGTTCTAT CTAAGAAAGT CCCCGAGCAG TTCGAGAAGT   2580

ATTCACTCTG GACCCTCGTC AAGTTCATCG GTGCATTTAA CCGCCCTGAG CTTGGTTACA   2640

TGCTCATTGG CTTGACTTTC TCGTTCCTTG CCGGTGGTGG TCAACCTACC CAGGCTTTTC   2700
```

-continued

```
TGTACGCCAA GGCAATTAGC ACGCTCTCGT TACCCGAATC AATGTTTCAC AAACTCAGGC    2760

ATGACGCGAA TTTCTGGTCC TTGATGTTCT TCGTGGTTGG AATTGCTCAA TTTATCAGCC    2820

TGTCTATCAA TGGTACAGCA TTTGCTATTT GTTCGGAGAG ACTCATTCGC CGAGCTAGAA    2880

GTCAAGCGTT TAGATCGATT CTTCGTCAGG ACATCTCATT TTTCGACAGG GAAGAGAACA    2940

GCACCGGTGC CTTGACGTCC TTCTTATCAA CAGAGACGAA GAATCTGTCG GGCGTTAGCG    3000

GAGTGACTCT CGGCACAATC ATCATGACTA GCACTACGCT TGGGGCGGCG ATGATCATTG    3060

CATTGGCGAT CGGATGGAAG CTGGCTCTGG TTTGCATTTC TGTCGTTCCA ATCCTTCTGG    3120

CATGCGGCTT CCTCAGATTC TACATGCTTG CTCAATTCCA GCAACGATCG AAGTCTGCCT    3180

ACGAAGGGTC TGCGAGCTAT GCTTGCGAAG CCACGTCAGC GATCCGCACT GTAGCATCAC    3240

TCACTCGCGA ACAAGATGTC TGGGGCGTTT ACCACGACCA GCTACAAAAA CAGGGACGGA    3300

AGAGTTTGAT CTCAGTGCTG AGATCCTCCC TGCTGTATGC CTCGTCGCAG GCATTGGTGT    3360

TTTTCTGCGT CGCTTTGGGC TTCTGGTATG GTGGTACACT TCTAGGCCAT CATGAGTACA    3420

GCATCTTCCG CTTCTTCGTC TGCTTTTCTG AGATTCTTTT TGGTGCGCAA TCAGCCGGAA    3480

CTGTCTTCTC TTTTGCCCCG GACATGGGTA AGGCAAAGAA TGCCGCTGCT CAATTCAAGA    3540

AACTCTTCGA CAGCAAGCCA ACCATTGACA TCTGGTCGGA TGAGGCGAG AAGTTGGAGT    3600

CTATGGAAGG CGAAATCGAA TTCCGGGACG TCCACTTTAG GTACCCAACG CGGCCGGAGC    3660

AGCCTGTTCT TCGAGGACTG AATTTGAGCG TGAAGCCTGG ACAATACATT GCCCTTGTTG    3720

GACCCAGTGG ATGCGGTAAG AGCACTACGA TTGCTCTGCT TGAGCGATTT TATGACGCAC    3780

TTGCTGGAGG GGTCTTCGTT GACGGAAAGG ACATTACCAA ACTCAATGTC AACTCATACC    3840

GCAGTTTCCT CTCCCTTGTC AGCCAAGAAC CTACTCTGTA TCAGGGTACC ATCAAGGAAA    3900

ATATCCTGCT TGGAGTCGAT AAGGATGACG TTTCGGAGGA GACTTTGATT AAGGTCTGCA    3960

AAGATGCCAA CATCTATGAT TTCGTTATGT CACTCCCGTA AGTTTACTGC CTCGCTGACT    4020

CCTTTCATGC CTGGCGGTTC TGCTAACATG CTACAACAGT GAGGGATTTG ACACCGTCGT    4080

TGGCAGCAAG GGAGGCATGT TGTCTGGTGG ACAAAAACAG CGTGTCGCCA TTGCTCGTGC    4140

CCTCCTGCGT GACCCCAAGG TCCTTCTTCT GGATGAAGCC ACATCTGCTC TTGACTCCGA    4200

ATCTGAGAAA GTCGTACAAG CTGCGCTGGA TGCTGCTGCC CGCGGGCGGA CAACGATTGC    4260

TGTTGCCCAC CGGCTGAGCA CCATTCAAAA CGCTGATATA ATTTACGTGT TCGACCAAGG    4320

CAAGATCGTC GAAAGTGGAA CGCACCACGA GTTGATTCGA AACAAGGGCC GGTATTACGA    4380

GCTGGTCAAT CTGCAGAGTC TCGGAAAGAC TCATTGATCA TTCCTTCCCC CTTCTTCTCA    4440

TGCTGTACCA ATGTACCAAT CTTCTTAATA TCTTCCTCCT CCCTGCTCAA TCATGTCATT    4500

CTTGGTGCTG AAAATACTGT GGATATACCA CCCCGCTTAT GTGTCTATGA TTCCCCTATA    4560

AAATTTTCAG CTTAATTGTC CTCGTCTTTG TACCTTATCC TCATCTTCGT TACTTAAAGC    4620

GCCGTATTTT TGGGCTGTCA TTGGAGTTGA TGGGTATCAC TTCTACTTGG GTGGGCGATA    4680

GGACAGAATC TTGCATCGCA GTCTTTTGCT AAGTGAACAC GATTTCAAAT TTATCATGTT    4740

CTATATAATT CGACGCATAT CCACATAGGG GGAACGAAGA ACAAGATGCA TCACAAACAG    4800
```

(2) INFORMATION FOR SEQ ID NO:4:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid

```
        (xi) SEQUENCE DESCRIPTION: SEQ ID NO:4:

GCTCGTTGAG AATGCGGCCA G                                                  21

(2) INFORMATION FOR SEQ ID NO:5:

(i) SEQUENCE CHARACTERISTICS:
           (A) LENGTH: 21 base pairs
           (B) TYPE: nucleic acid
           (C) STRANDEDNESS: single
           (D) TOPOLOGY: linear (ii) MOLECULE TYPE: other nucleic acid (xi) SEQUENCE DESCRIPTION: SEQ ID NO:5:

ACTTGGTATC CAAAGCTGAT G                                                  21

(2) INFORMATION FOR SEQ ID NO:6:

(i) SEQUENCE CHARACTERISTICS:
           (A) LENGTH: 28 base pairs
           (B) TYPE: nucleic acid
           (C) STRANDEDNESS: single
           (D) TOPOLOGY: linear (ii) MOLECULE TYPE: other nucleic acid (xi) SEQUENCE DESCRIPTION: SEQ ID NO:6:

GCGCGGATCC GCAACATGCC TGCGCCTG                                           28

(2) INFORMATION FOR SEQ ID NO:7:

(i) SEQUENCE CHARACTERISTICS:
           (A) LENGTH: 21 base pairs
           (B) TYPE: nucleic acid
           (C) STRANDEDNESS: single
           (D) TOPOLOGY: linear (ii) MOLECULE TYPE: other nucleic acid (xi) SEQUENCE DESCRIPTION: SEQ ID NO:7:

GGAATGATTA ATGAGTCTTT C                                                  21

(2) INFORMATION FOR SEQ ID NO:8:

(i) SEQUENCE CHARACTERISTICS:
           (A) LENGTH: 34 base pairs
           (B) TYPE: nucleic acid
           (C) STRANDEDNESS: single
           (D) TOPOLOGY: linear (ii) MOLECULE TYPE: other nucleic acid (xi) SEQUENCE DESCRIPTION: SEQ ID NO:8:

TACCCATACG ACGTCCCAGA CTACGCTTGA TAAT                                    34

(2) INFORMATION FOR SEQ ID NO:9:

(i) SEQUENCE CHARACTERISTICS:
           (A) LENGTH: 36 base pairs
           (B) TYPE: nucleic acid
           (C) STRANDEDNESS: single
           (D) TOPOLOGY: linear (ii) MOLECULE TYPE: other nucleic acid (xi) SEQUENCE DESCRIPTION: SEQ ID NO:9:

CTAGATTATC AAGCGTAGTC TGGGACGTCG TATGGG                                  36
```

MULTIPLE DRUG RESISTANCE GENE OF *ASPERGILLUS FUMIGATUS*

TECHNICAL FIELD OF THE INVENTION

This invention relates to recombinant DNA technology. In particular, the invention concerns the cloning of nucleic acid encoding a multiple drug resistance protein of *Aspergillus fumigatus*.

BACKGROUND OF THE INVENTION

Multiple drug resistance (MDR) mediated by the human mdr-1 gene product was initially recognized during the course of developing regimens for cancer chemotherapy (Fojo et al., 1987, *Journal of Clinical Oncology* 5:1922–1927). A multiple drug resistant cancer cell line exhibits resistance to high levels of a large variety of cytotoxic compounds. Frequently these cytotoxic compounds will have no common structural features nor will they interact with a common target within the cell. Resistance to these cytotoxic agents is mediated by an outward directed, ATP-dependent pump encoded by the mdr-1 gene. By this mechanism, toxic levels of a particular cytotoxic compound are not allowed to accumulate within the cell.

MDR-like genes have been identified in a number of divergent organisms including numerous bacterial species, the fruit fly *Drosophila melanogaster*, *Plasmodium falciparum*, the yeast *Saccharomyces cerevisiae*, *Caenorhabditis elegans*, *Leishmania donovanii*, marine sponges, the plant *Arabidopsis thaliana*, as well as *Homo sapiens*. Extensive searches have revealed several classes of compounds that are able to reverse the MDR phenotype of multiple drug resistant human cancer cell lines rendering them susceptible to the effects of cytotoxic compounds. These compounds, referred to herein as "MDR inhibitors", include for example, calcium channel blockers, antiarrhythmics, antihypertensives, antibiotics, antihistamines, immuno-suppressants, steroid hormones, modified steroids, lipophilic cations, diterpenes, detergents, antidepressants, and antipsychotics (Gottesman and Pastan, 1993, *Annual Review of Biochemistry* 62:385–427). Clinical application of human MDR inhibitors to cancer chemotherapy has become an area of intensive focus for research.

On another front, the discovery and development of antifungal compounds for specific fungal species has also met with some degree of success. Candida species represent the majority of fungal infections, and screens for new antifungal compounds have typically been designed to discover anti-Candida compounds. During development of antifungal agents, activity has generally been optimized based on activity against *Candida albicans*. As a consequence, these anti-Candida compounds frequently do not possess clinically significant activity against other fungal species such as *Aspergillus fumigatus*. However, it is interesting to note that at higher concentrations some anti-Candida compounds are able to kill Aspergillus fungal species. This suggests that the antifungal target(s) of these anti-Candida compounds is present in Aspergillus as well. Such results indicate that Aspergillus may possess a natural mechanism of resistance that permits them to survive in clinically relevant concentrations of antifungal compounds. Until the present invention, such a general mechanism of resistance to antifungal compounds in *Aspergillus fumigatus* has remained undescribed.

SUMMARY OF THE INVENTION

The invention provides, inter alia, isolated nucleic acid molecules that comprise nucleic acid encoding a multiple drug resistance protein from *Aspergillus fumigatus*, referred to herein as AfuMDR1, vectors encoding AfuMDR1, and host cells transformed with these vectors.

In another embodiment, the invention provides a method for determining the fungal MDR inhibition activity of a compound which comprises:

a) placing a culture of fungal cells, transformed with a vector capable of expressing AfuMDR1, in the presence of:
  (i) an antifungal agent to which said fungal cell is resistant, but to which said fungal cell is sensitive in its untransformed state;
  (ii) a compound suspected of possessing fungal MDR inhibition activity; and
b) determining the fungal MDR inhibition activity of said compound by measuring the ability of the antifungal agent to inhibit the growth of said fungal cell.

BRIEF DESCRIPTION OF THE FIGURES

The restriction enzyme site and function maps presented in the accompanying drawings are approximate representations of plasmids pPSM6, pPSM32, pPSM41, pPSM40, pPSM43, and pPSM42, discussed herein. The restriction enzyme site information is not exhaustive. There may be more restriction enzyme sites of a given type on the vectors than actually shown on the maps.

DETAILED DESCRIPTION OF THE INVENTION

Figure 1:
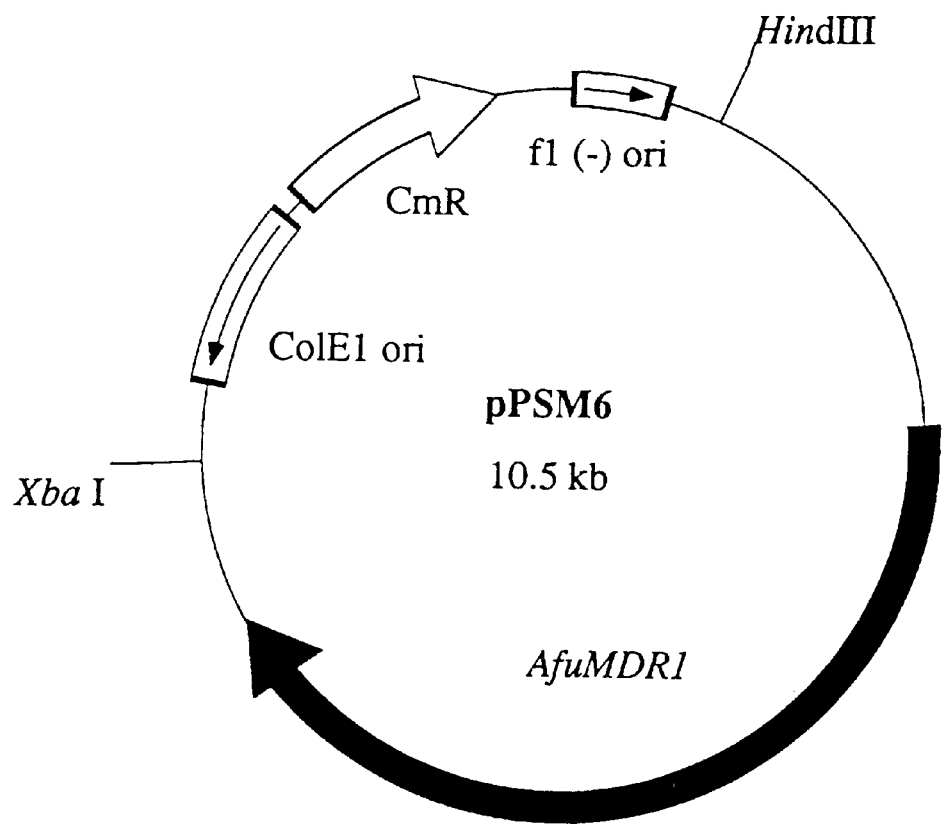
FIG. 1—A restriction enzyme site and function map of plasmid pPSM6.

The present invention provides isolated nucleic acid molecules that comprise a nucleic acid sequence encoding AfuMDR1. The amino acid sequence of AfuMDR1 is provided in the Sequence Listing as SEQ ID NO: 2. The cDNA (complementary deoxyribonucleic acid) sequence encoding AfuMDR1 is provided in the Sequence Listing as SEQ ID NO: 1. The genomic sequence encoding AfuMDR1 is provided as SEQ ID NO: 3.

Those skilled in the art will recognize that the degenerate nature of the genetic code enables one to construct many different nucleic acid sequences that encode the amino acid sequence of SEQ ID NO: 2. The cDNA sequence depicted by SEQ ID NO: 1 is only one of many possible AfuMDR1-encoding sequences. Consequently, the constructions described below and in the accompanying examples for the preferred nucleic acid molecules, vectors, and transformants of the invention are illustrative and are not intended to limit the scope of the invention.

All nucleotide and amino acid abbreviations used in this disclosure are those accepted by the United States Patent and Trademark Office as set forth in 37 C.F.R. §1.822(b)(1994).

The term "vector" refers to any autonomously replicating or integrating agent, including but not limited to plasmids, cosmids, and viruses (including phage), comprising a nucleic acid molecule to which one or more additional nucleic acid molecule can be added. Included in the definition of "vector" is the term "expression vector". Vectors are used either to amplify and/or to express deoxyribonucleic acid (DNA), either genomic or cDNA, or RNA (ribonucleic acid) which encodes AfuMDR1, or to amplify DNA or RNA that hybridizes with DNA or RNA encoding AfuMDR1.

The term "expression vector" refers to vectors which comprise a transcriptional promoter (hereinafter "promoter") and other regulatory sequences positioned to drive expression of a DNA segment that encodes AfuMDR1. Expression vectors of the present invention are replicable DNA constructs in which a DNA sequence encoding AfuMDR1 is operably linked to suitable control sequences capable of effecting the expression of AfuMDR1 in a suitable host. Such control sequences include a promoter, an optional operator sequence to control transcription, a sequence encoding suitable mRNA ribosomal binding sites, and sequences which control termination of transcription and translation. DNA regions are operably linked when they are functionally related to each other. For example, a promoter is operably linked to a DNA coding sequence if it controls the transcription of the sequence, or a ribosome binding site is operably linked to a coding sequence if it is positioned so as to permit translation.

The term "MDR inhibition activity" refers to the ability of a compound to inhibit the MDR activity of a host cell, thereby increasing the antifungal activity of an antifungal compound against said host cell.

In the present invention, AfuMDR1 may be synthesized by host cells transformed with vectors that provide for the expression of DNA encoding AfuMDR1. The DNA encoding AfuMDR1 may be the natural sequence or a synthetic sequence or a combination of both ("semi-synthetic sequence"). The in vitro or in vivo transcription and translation of these sequences results in the production of AfuMDR1. Synthetic and semi-synthetic sequences encoding AfuMDR1 may be constructed by techniques well known in the art. See Brown et al. (1979) *Methods in Enzymology*, Academic Press, N.Y., 68:109–151. AfuMDR1-encoding DNA, or portions thereof, may be generated using a conventional DNA synthesizing apparatus such as the Applied Biosystems Model 380A, 380B, 384 or 3848 DNA synthesizers (commercially available from Applied Biosystems, Inc., 850 Lincoln Center Drive, Foster City, Calif. 94404).

Owing to the natural degeneracy of the genetic code, the skilled artisan will recognize that a sizable yet definite number of nucleic acid sequences may be constructed which encode AfuMDR1. All such nucleic acid sequences are provided by the present invention. These sequences can be prepared by a variety of methods and, therefore, the invention is not limited to any particular preparation means. The nucleic acid sequences of the invention can be produced by a number of procedures, including DNA synthesis, cDNA cloning, genomic cloning, polymerase chain reaction (PCR) technology, or a combination of these approaches. These and other techniques are described by Maniatis, et al. *Molecular Cloning: A Laboratory Manual*, Cold Spring Harbor Press, Cold Spring Harbor Laboratory, Cold Spring Harbor, N.Y. (1989), or *Current Protocols in Molecular Biology* (F. M. Ausubel et al., 1989 and supplements). The contents of both of these references are incorporated herein by reference.

In another aspect, this invention provides the genomic DNA encoding AfuMDR1. This DNA sequence is preferably obtained from plasmid pPSM6, described in Example 1. A restriction site and function map of pPSM6 is provided as FIG. 1 of the drawings. Plasmid pPSM6 comprises the ColE1 origin of replication (ColE1) which allows replication in *Escherichia coli* host cells, and the chloramphenicol resistance gene (CmR) for selection of *E. coli* cells transformed with the plasmid grown in the presence of chloramphenicol. The plasmid also contains the T7 promoter and the origin of replication from the f1 filamentous phage. The genomic DNA encoding AfuMDR1 can be obtained from plasmid pPSM6 on an approximately 7.1 kilobase pair HindIII/XbaI restriction enzyme fragment.

To effect the translation of AfuMDR1-encoding mRNA, one inserts the natural, synthetic, or semi-synthetic AfuMDR1-encoding DNA sequence into any of a large number of appropriate expression vectors through the use of appropriate restriction endonucleases and DNA ligases. Synthetic and semi-synthetic AfuMDR1-encoding DNA sequences can be designed, and natural AfuMDR1-encoding nucleic acid can be modified, to possess restriction endonuclease cleavage sites to facilitate isolation from and integration into these vectors. Particular restriction endonucleases employed will be dictated by the restriction endonuclease cleavage pattern of the expression vector utilized. Restriction enzyme sites are chosen so as to properly orient the AfuMDR1-encoding DNA with the control sequences to achieve proper in-frame translation of the AfuMDR1 molecule. The AfuMDR1-encoding DNA must be positioned so as to be in proper reading frame with the promoter and ribosome binding site of the expression vector, both of which are functional in the host cell in which AfuMDR1 is to be expressed.

Expression of AfuMDR1 in yeast cells, such as *Saccharomyces cerevisiae* is preferred. Suitable promoter sequences for use with yeast hosts include the promoters for 3-phosphoglycerate kinase (found on plasmid pAP12BD (ATCC 53231) and described in U.S. Pat. No. 4,935,350, Jun. 19, 1990) or other glycolytic enzymes such as enolase (found on plasmid pAC1 (ATCC 39532)), glyceraldehyde-3-phosphate dehydrogenase (derived from plasmid pHc-GAPC1 (ATCC 57090, 57091)), hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Inducible yeast promoters have the additional advantage of transcription controlled by growth conditions. Such promoters include the promoter regions for alcohol dehydrogenase 2, isocytochrome C, acid phosphotase, degradative enzymes associated with nitrogen metabolism, metallothionein (contained on plasmid vector pCL28XhoLHBPV (ATCC 39475), U.S. Pat. No. 4,840, 896), glyceraldehyde 3-phosphate dehydrogenase, and enzymes responsible for maltose and galactose utilization (GAL1 found on plasmid pRY121 (ATCC 37658) and on plasmid pPSM41, described below). Suitable vectors and promoters for use in yeast expression are further described by R. Hitzeman et al., in European Patent Publication No. 73,657A. Yeast enhancers such as the UAS Gal enhancer from *Saccharomyces cerevisiae* (found in conjunction with the CYC1 promoter on plasmid YEpsec—hI1beta, (ATCC 67024)), also are advantageously used with yeast promoters.

A variety of expression vectors useful in the present invention are well known in the art. For expression in Saccharomyces, the plasmid YRp7, for example, (ATCC-40053, Stinchcomb et al., 1979, *Nature* 282:39; Kingsman et al., 1979, *Gene* 7:141; Tschemper et al., 1980, *Gene* 10:157) is commonly used. This plasmid contains the trp gene which provides a selection marker for a mutant strain of yeast lacking the ability to grow in tryptophan, for example ATCC no. 44076 or PEP4-1 (Jones, 1977, *Genetics* 85:12).

Expression vectors useful in the expression of AfuMDR1 can be constructed by a number of methods. For example, the cDNA sequence encoding AfuMDR1 can be synthesized using DNA synthesis techniques such as those described above. Such synthetic DNA can be synthesized to contain cohesive ends that allow facile cloning into an appropriately digested expression vector. For example, the cDNA encoding AfuMDR1 can be synthesized to contain BamHI/XbaI cohesive ends. Such a synthetic DNA fragment can be ligated into a BamHI/XbaI-digested expression vector such as pYES-2 (Invitrogen Corp., San Diego Calif. 92121). The resultant plasmid is designated herein as pPSM41. Plasmid pPSM41 is useful for the expression of AfuMDR1 in *Saccharomyces cerevisiae*.

A plasmid related to pPSM41 can be constructed in the following manner. Logarithmic phase *Aspergillus fumigatus* mycelia are disrupted by grinding under liquid nitrogen according to the procedure of Minuth et al., 1982 (Current Genetics 5:227–231). *Aspergillus fumigatus* mRNA is preferably isolated from the disrupted mycelia using the Quick-Prep™ mRNA Purification Kit (Pharmacia Biotech) according to the instructions of the manufacturer. cDNA is produced from the isolated mRNA using the TimeSaver® cDNA Synthesis Kit (Pharmacia Biotech) using oligo (dT) according to the procedure described by the manufacturer. In this process an EcoRI/NotI adapter (Stratagene, Inc.) is ligated to each end of the double stranded cDNA. The adapter modified cDNA is ligated into the vector Lambda Zap$^R$II® using the Predigested Lambda Zap$^R$II®/EcoRI/CIAP Cloning Kit (Stratagene, Inc.) according to the instructions of the manufacturer to create a cDNA library.

The library is screened for full-length cDNA encoding AfuMDR1 using a $^{32}$P-radiolabeled fragment of the AfuMDR1 gene. This radiolabeled fragment is produced from the AfuMDR1 genomic DNA present in plasmid pPSM6. Utilizing the polymerase chain reaction (Gene Amp® Kit, Perkin Elmer Cetus, Norwalk, Conn.) and primers based upon the sequence presented as SEQ ID No. 1, a AfuMDR1 radiolabeled fragment is obtained. This radiolabeled fragment is used to probe the *Aspergillus fumigatus* cDNA library using standard hybridization techniques (Maniatis et al. 1992). In this manner, a full-length cDNA clone is recovered from the *Aspergillus fumigatus* cDNA library. A full-length cDNA clone recovered from the library is removed from the Lambda Zap$^R$II vector by digestion with the restriction endonuclease NotI which produces an approximately 4100 base pair DNA fragment encoding AfuMDR1. The vector DNA fragment and the desired approximately 4100 base pair NotI DNA restriction fragment are separated by agarose gel electrophoresis. The desired approximately 4100 base pair NotI DNA fragment encoding AfuMDR1 is isolated by cutting out that portion of the agarose gel containing the fragment and electroeluting the DNA using a Centrilutor™ Micro-electroeluter (Amicon, Inc.) according to the manufacturer's instructions. The isolated approximately 4100 base pair NotI restriction fragment encoding AfuMDR1 is ligated to NotI digested pYES2 vector DNA. The correct orientation of the insert DNA is screened for by restriction endonuclease digestion using asymmetric sites located with the coding region and the flanking vector. The resultant plasmid is useful for the expression of AfuMDR1 in *Saccharomyces cerevisiae*.

Figure 2:
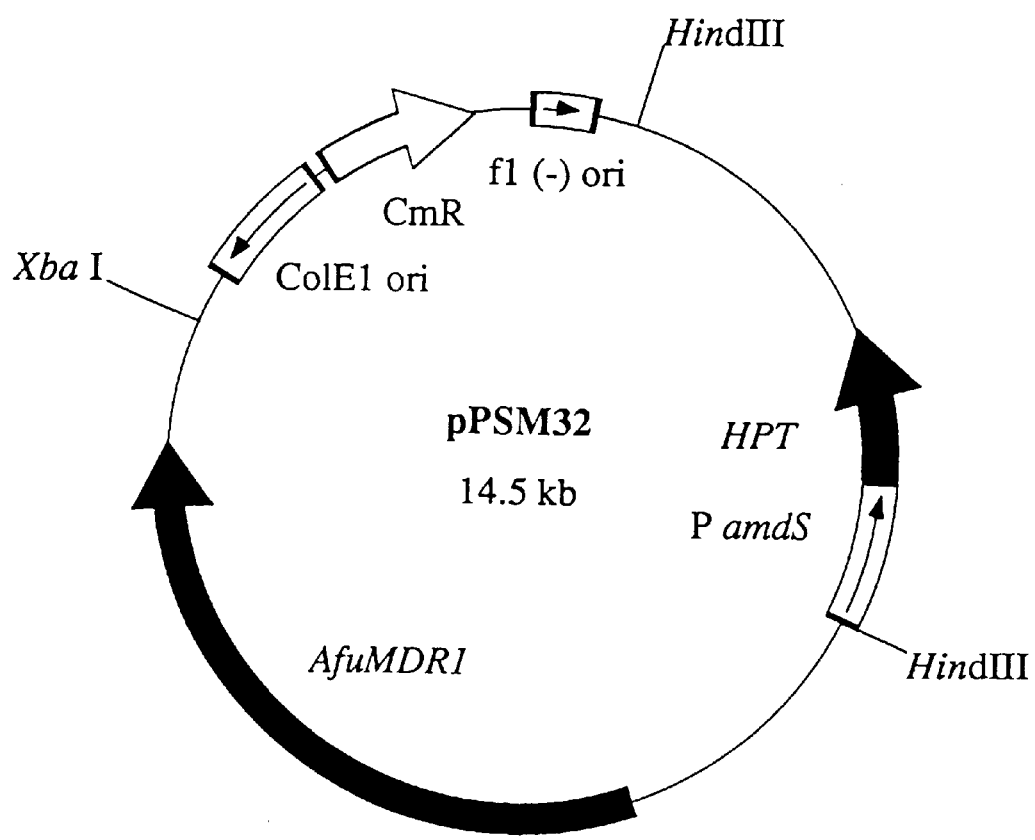
FIG. 2—A restriction enzyme site and function map of plasmid pPSM32.

A representation of plasmid pPSM41 is provided as FIG. 2. As noted above, this plasmid contains the AfuMDR1-encoding DNA operably linked to the *Saccharomyces cerevisiae* GAL1 promoter (P Gal1). Plasmid pPSM41 also comprises the yeast transcription terminator cyc1 (T cyc1) located in a position 3' to the AfuMDR1-encoding DNA. Plasmid pPSM41 further comprises the ColE1 origin of replication (ColE1) which allows replication in *Escherichia coli* host cells, and the ampicillin resistance gene (Amp) for selection of *E. coli* cells transformed with the plasmid grown in the presence of ampicillin. Plasmid pPSM41 further comprises the yeast 2$\mu$ origin of replication (2$\mu$ ori) allowing replication in yeast host cells, the yeast URA3 gene for selection of *S. cerevisiae* cells transformed with the plasmid grown in a medium lacking uracil, and the origin of replication from the f1 filamentous phage.

In a preferred embodiment of the invention *Saccharomyces cerevisiae* INVSc1 or INVSc2 cells (Invitrogen Corp., Sorrento Valley Blvd., San Diego Calif. 92121) are employed as host cells, but numerous other cell lines are available for this use. The transformed host cells are plated on an appropriate medium under selective pressure (minimal medium lacking uracil). The cultures are then incubated for a time and temperature appropriate to the host cell line employed.

The techniques involved in the transformation of yeast cells such as *Saccharomyces cerevisiae* cells are well known in the art and may be found in such general references as Ausubel et al., *Current Protocols in Molecular Biology* (1989), John Wiley & Sons, New York, N.Y. and supplements. The precise conditions under which the transformed yeast cells are cultured is dependent upon the nature of the yeast host cell line and the vectors employed.

Figure 4:
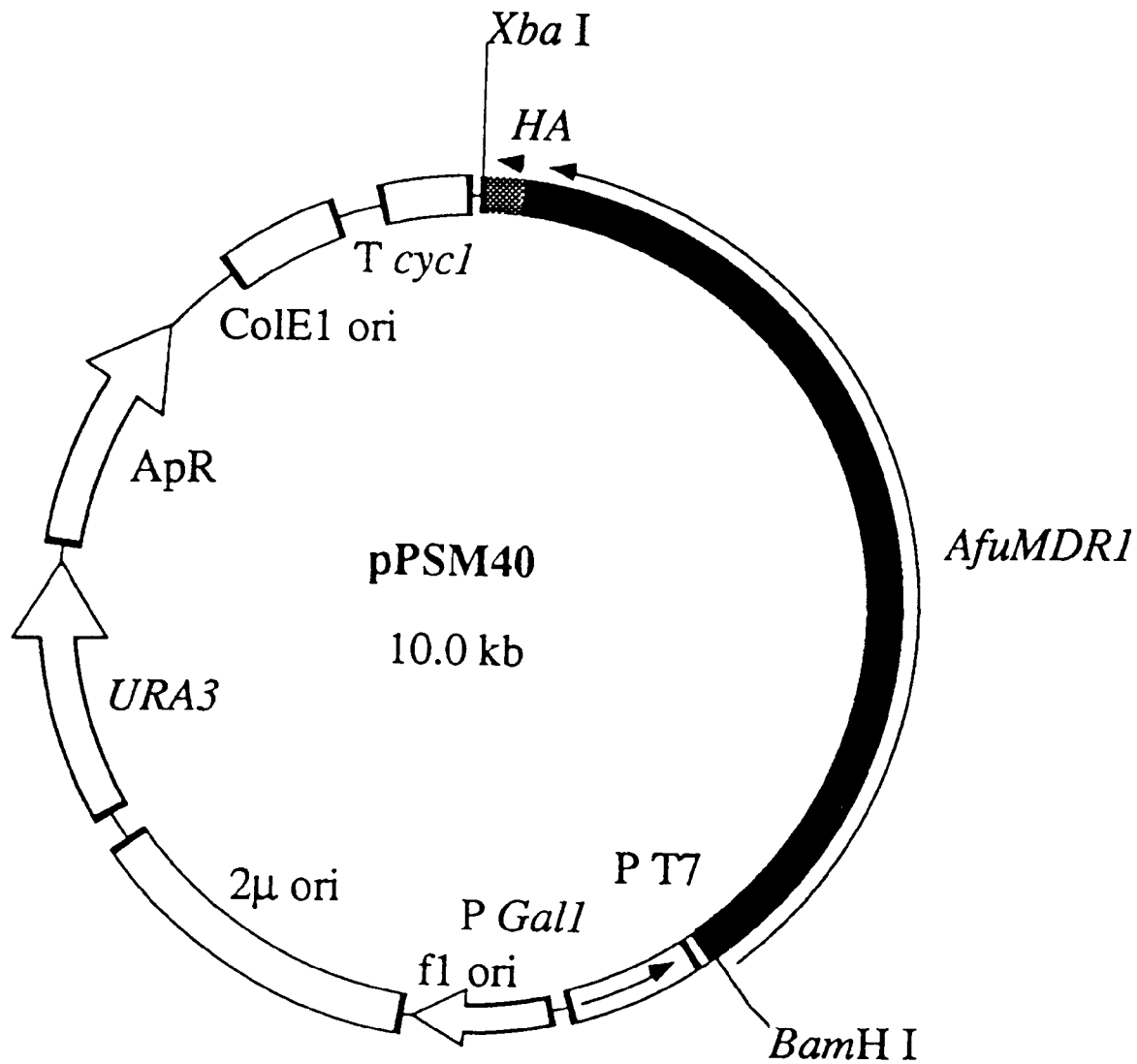
FIG. 4—A restriction enzyme site and function map of plasmid pPSM40.

In another application of this invention, plasmid pPSM40 (FIG. 4) is constructed which is similar to plasmid pPSM41 with the exception that a hemagglutinin tag (described in Example 4) is added to the 3' end of AfuMDR1. This immunological molecular handle is useful for protein purification, verification of protein production and cellular localization of the protein encoded by AfuMDR1.

Another preferred embodiment of this invention involves large scale production of AfuMDR1-encoded protein by expression in baculovirus. Two plasmids were constructed which permit expression of AfuMDR1 in baculovirus. The first plasmid, pPSM43 (FIG. 5), contains the polyhedron promoter (PpolH) of the *Autographa californica* nuclear polyhedrosis virus attached to AfuMDR1 plus other factors which allow infection of insect cells. The second plasmid (pPSM42, FIG. 6), constructed for baculovirus expression studies was nearly identical to pPSM43 except that it contained the hemagglutinin tag attached to the 3' end of AfuMDR1.

Nucleic acid, either RNA or DNA, which encodes AfuMDR1, or a portion thereof, is also useful in producing nucleic acid molecules useful in diagnostic assays for the detection of AfuMDR1 mRNA, AfuMDR1 cDNA, or AfuMDR1 genomic DNA. Further, nucleic acid, either RNA or DNA, which does not encode AfuMDR1, but which nonetheless is capable of hybridizing with AfuMDR1-encoding DNA or RNA is also useful in such diagnostic assays. These nucleic acid molecules may be covalently labeled by known methods with a detectable moiety such as a fluorescent group, a radioactive atom or a chemiluminescent group. The labeled nucleic acid is then used in conventional hybridization assays, such as Southern or Northern hybridization assays, or polymerase chain reaction assays (PCR), to identify hybridizing DNA, cDNA, or RNA molecules. PCR assays may also be performed using unlabeled nucleic acid molecules. Such assays may be employed to identify AfuMDR1 vectors and transformants and in in vitro diagnosis to detect AfuMDR1-like mRNA, cDNA, or genomic DNA from other organisms.

U.S. patent application Ser. No. 08/111680, now abandoned, the entire contents of which are hereby incorporated herein by reference, describes the use of combination therapy involving an antifungal agent possessing a proven spectrum of activity, with a fungal MDR inhibitor to treat fungal infections. This combination therapy approach enables an extension of the spectrum of antifungal activity for a given antifungal compound which previously had only demonstrated limited clinically relevant antifungal activity. Similarly, compounds with demonstrated antifungal activity can also be potentiated by a fungal MDR inhibitor such that the antifungal activity of these compounds is extended to previously resistant species. To identify compounds useful in such combination therapy the present invention provides an assay method for identifying compounds with *Aspergillus fumigatus* MDR inhibition activity. Host cells that express AfuMDR1 provide an excellent means for the identification of compounds useful as inhibitors of *Aspergillus fumigatus* MDR activity. Generally, the assay utilizes a culture of a fungal cell transformed with a vector which provides expression of AfuMDR1. The expression of AfuMDR1 by the host cell enables the host cell to grow in the presence of an antifungal compound to which the fungal cell is sensitive to in the untransformed state. Thus, the transformed fungal cell culture is grown in the presence of i) an antifungal agent to which the untransformed fungal cell is sensitive, but to which the transformed host cell is resistant, and ii) a compound that is suspected of being an MDR inhibitor. The effect of the suspected MDR inhibitor is measured by testing for the ability of the antifungal compound to inhibit the growth of the transformed fungal cell. Such inhibition will occur if the suspected *Aspergillus fumigatus* MDR inhibitor blocks the ability of AfuMDR1 to prevent the antifungal compound from acting on the fungal cell. An illustrative example of such an assay is provided in Example 7.

In order to illustrate more fully the operation of this invention, the following examples are provided, but are not to be construed as a limitation on the scope of the invention.

EXAMPLE 1

Source of the AfuMDR1 encoding Genomic DNA of *Aspergillus fumigatus*

Construction of plasmid pPSM6 containing AfuMDR1

An approximately 7100 bp HindIII-XbaI fragment of genomic DNA containing AfuMDR1 from *Aspergillus fumigatus* may be obtained in the following manner. Some adjustment may be required if a different strain of *Aspergillus fumigatus* is used than that used by Applicants, which was 10AF/86/10 (Denning and Stevens, *Antimicrob. Agents and Chemother.* 35:1329–1333). Total DNA is isolated from logarithmic phase *Aspergillus fumigatus* mycelia by grinding under liquid nitrogen according to the procedure of Minuth et al., 1982 (*Current Genetics* 5:227–231). The DNA is cleaved with the restriction endonucleases HindIII and XbaI, electrophoresed through a 0.8% agarose gel and the DNA fragments produced corresponding to approximately 6500 to 7500 bp are isolated by electroelution (Centriluter™ Micro-electroeluter, Amicon, Inc.). The isolated fragments are ligated into the commercially available plasmid vector pBC SK(−) (Stratagene Inc., LaJolla, Calif.) after digestion with HindIII and XbaI. Transformant colonies produced by this cloning process are screened for the presence of AfuMDR1 using a hybridization probe comprised of a significant portion of the AfuMDR1 gene produced by PCR using the following primers according to the manufacturers instructions: 5'-GCTCGTTGAGAATGCGGCCAG-3' (SEQ ID NO: 4) and 5'-ACTTGGTATCCAAAGCTGATG-3' (SEQ ID NO: 5). The resultant plasmid, pPSM6, is subjected to restriction endonuclease digestion and analysis by agarose gel electrophoresis. A representation of plasmid pPSM6 is provided as FIG. 1.

EXAMPLE 2

Expression of AfuMDR1 in *Aspergillus montevidensis*

*Aspergillus montevidensis* (ATTCC #10077) is susceptible to a wide range of antifungal compounds, suggesting the lack of an effective efflux mechanism(s) for such compounds. Functional expression of AfuMDR1 in such a strain will produce an antifungal resistant phenotype and provides a useful strain for screening for inhibition of AfuMDR1. Expression of AfuMDR1 in such a related Aspergillus species avoids problems presented by the presence of introns within this gene (i.e. splicing of introns should be similar in these species) and promoter recognition.

Construction of plasmid pPSM32 for the expression of AfuMDR1 in *Aspergillus montevidensis*

The present example utilizes a selectable marker for transformation of *Aspergillus montevidensis* comprised of the hygromycin B phosphotransferase (HPT) gene (Kaster et al., 1984, *Current Genetics,* 8:353–358) operably linked to the *Aspergillus nidulans* amds promoter (P-amdS) (Hynes et al., 1983, *Molecular and Cellular Biology,* 3:1430–1439). Those skilled in the art will recognize that this promoter/selectable marker combination may be assembled in a number of ways. In one instance, PCR is used to generate P-amdS and HPT independently which are ligated together to form the operable selectable marker with for example HindIII restriction sites at both termini. In our case this process produces an approximately 4,000 bp HindIII fragment carrying the operable selectable marker.

Plasmid pPSM6 is linearized by restriction endonuclease digestion with HindIII. The resultant approximately 10,500 bp DNA fragment is ligated to the approximately 4,000 base pair HindIII DNA fragment encoding HPT. The resultant plasmid, pPSM32, is subjected to restriction endonuclease digestion and analysis by agarose gel electrophoresis. Plasmid pPSM32, represented in FIG. 2, is suitable for the expression of AfuMDR1 in *Aspergillus montevidensis.*

EXAMPLE 3

Expression of the AfuMDR1 gene in *Saccharomyces cerevisiae*

Expression of the AfuMDR1 gene in eukaryotic cells other than Aspergillus (or other closely related species capable of utilizing endogenous AfuMdR1 promoter and terminator sequences) is accomplished by the removal of endogenous AfuMDR1 promoter and terminator DNA sequences and their replacement with promoter and terminator DNA sequences compatible with gene expression in the host of choice.

Construction of plasmid pPSM41 for expression of AfuMDR1 in *Saccharomyces cerevisiae*

Total *A. fumigatus* mRNA is isolated from disrupted mycelia using the QuickPrep™ mRNA purification Kit (Pharmacia Biotech) using oligo (dT) according to the procedure described by the manufacturer. First strand cDNA synthesis is accomplished using the Superscrip™ Preamplification System (GibcoBRL/Life Technologies) according to the procedure described by the manufacturer. The resultant cDNA is used as template in an amplification process using the polymerase chain reaction. Utilizing cloned Pfu DNA Polymerase (Stratagene) in the polymerase chain reaction and the following primers: TBN-76 (5'-GCGCGGATCCGCAACATGCCTGCGCCTG-3') (SEQ ID NO: 6) and TBN-77 (5'-GGAATGATTAATGAGTCTTTC-3') (SEQ ID NO: 7), an approximately 4,100 base pair DNA fragment encoding AfuMDR1 is amplified. The resultant fragment is subjected to restriction endonuclease digestion with BamHI and XbaI, and subjected to agarose gel electrophoresis. The desired approximately 4100 base pair BamHI-XbaI DNA fragment encoding AfuMDR1 is isolated by excising that portion of the agarose gel containing the fragment and electroeluting the DNA using a Centriluter™ Micro-electroeluter (Amicon, Inc.) according to the manufacturer's instructions. The resultant approximately 4,100 base pair BamHI-XbaI DNA fragment is ligated to BamHI and XbaI-digested plasmid pYES2 vector DNA (Invitrogen Corp., San Diego, Calif.). The resultant plasmid, pPSM41, is useful for the expression of AfuMDR1 in *Saccharomyces cerevisiae*.

Figure 3:
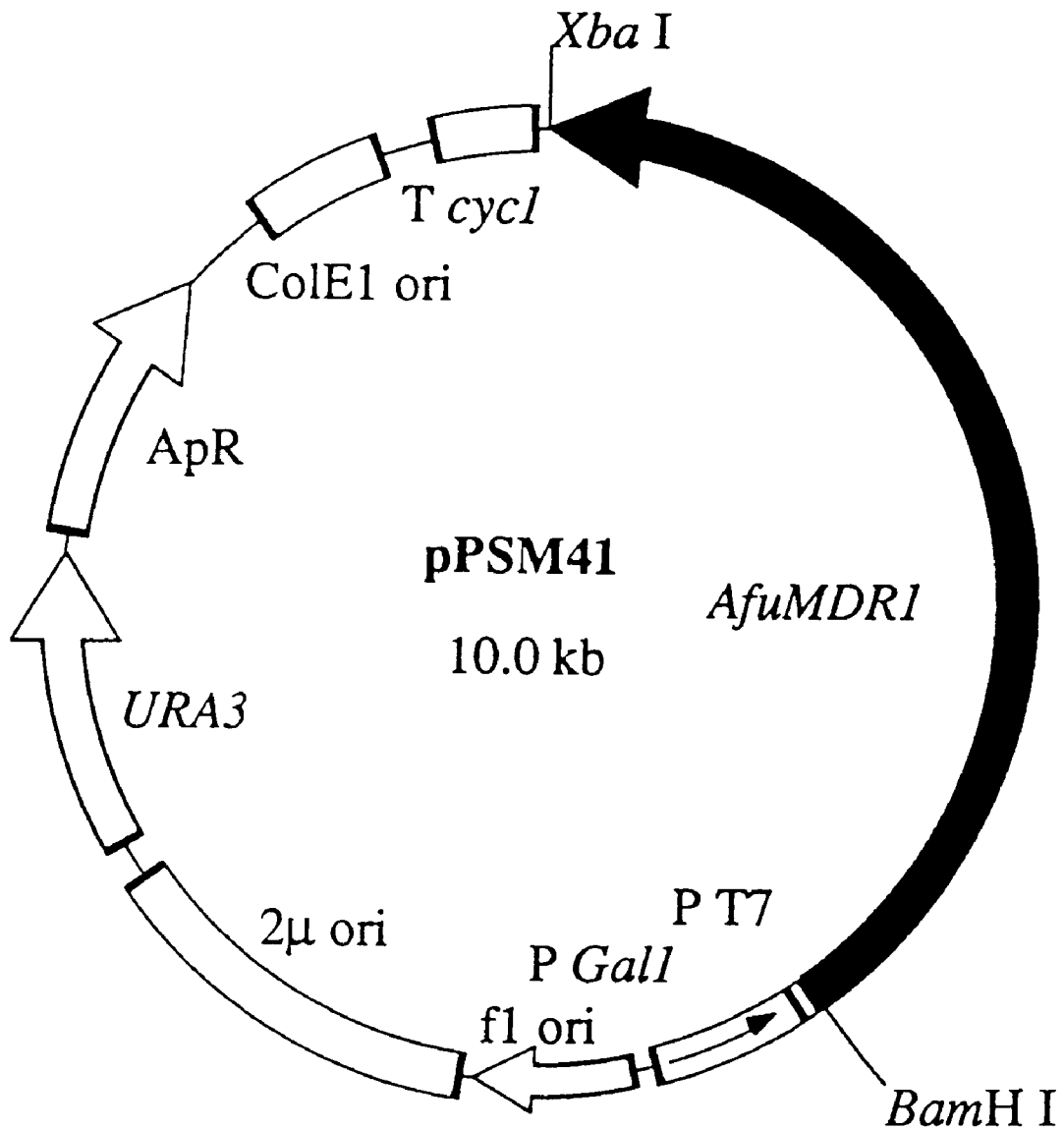
FIG. 3—A restriction enzyme site and function map of plasmid pPSM41.

A representation of plasmid pPSM41 is provided as FIG. 3. As noted above, this plasmid contains the AfuMDR1-encoding DNA operably linked to the *Saccharomyces cerevisiae* GAL1 promoter (P Gal1). Plasmid pPSM41 also comprises the yeast transcription terminator cyc1 (T cyC1) located in a position 3' to the AfuMDR1-encoding DNA. Plasmid pPSM41 further comprises the ColE1 origin of replication (ColE1) which allows replication in *Escherichia coli* host cells, and the ampicillin resistance gene (Amp) for selection of *E. coli* cells transformed with the plasmid grown in the presence of ampicillin. Plasmid pPSM41 further comprises the yeast $2\mu$ origin of replication ($2\mu$ ori) allowing replication in yeast host cells, the yeast URA3 gene for selection of *S. cerevisiae* cells transformed with the plasmid grown in a medium lacking uracil, and the origin of replication from the f1 filamentous phage.

In a preferred embodiment of the invention *Saccharomyces cerevisiae* INVSc1 or INVSc2 cells (Invitrogen Corp., Sorrento Valley Blvd., San Diego Calif. 92121) are employed as host cells, but numerous other cell lines are available for this use. The transformed host cells are plated on an appropriate medium under selective pressure (minimal medium lacking uracil). The cultures are then incubated for a time and temperature appropriate to the host cell line employed.

The techniques involved in the transformation of yeast cells such as *Saccharomyces cerevisiae* cells are well known in the art and may be found in such general references as Ausubel et al., *Current Protocols in Molecular Biology* (1989), John Wiley & Sons, New York, N.Y. and supplements. The precise conditions under which the transformed yeast cells are cultured is dependent upon the nature of the yeast host cell line and the vectors employed.

*Saccharomyces cerevisiae* INVSc1 cells (Invitrogen Corp., San Diego Calif. 92191) are transformed with the plasmid pPSM41 by the technique described by J. D. Beggs, 1988, *Nature* 275:104–109). The transformed yeast cells are grown in a broth medium containing YNB/CSM-Ura/raf (YNB/CSM-Ura [Yeast Nitrogen Base (Difco Laboratories, Detroit, Mich.) supplemented with CSM-uRA (Bio 101, Inc.)] supplemented with 4% raffinose) at 28° C. in a shaker incubator until the culture is saturated. To induce expression of AfuMDR1, a portion of the culture is used to inoculate a flask containing YNB/CSM-Ura medium supplemented with 2% galactose (YNB/CSM-Ura/gal) rather than raffinose as the sole carbon source. The inoculated flask is incubated at 28° C. for about 16 hours.

EXAMPLE 4

Expression of the AfuMDR1/HA fusion in *Saccharomyces cerevisiae*

During the course of expression studies it would be useful to have an easily detected molecular handle attached to the protein expressed by AfuMDR1. This molecular tag would useful in detection of protein produced, purification of protein, and localization of protein within the cell expressing AfuMDR1.

Construction of plasmid pPSM40 containing a HA tag

To facilitate the detection and purification of the protein encoded by AfuMDR1, a gene encoding a fusion protein is constructed. A sequence encoding a peptide antigenic to a commercially available antibody may effectively be added in-frame to either the NH-terminus or the COOH-terminus of the encoded AfuMDR1 sequence. In the present example, a COOH-terminal fusion to AfuMDR1 using an encoded hemagglutanin (HA) flu epitope tag YPYDVPDYA is described, however, the specific constructions described herein are in no way intended to limit the scope of the invention. Polyclonal Rabbit Antibody, HA.11, is purchased from Berkeley Antibody Company (Richmond, Calif.), and may be used for epitope tagging and protein surveilance according to the recommendations of the manufacturer.

The approximately 4100 base pair BamHI-XbaI DNA fragment encoding Afu-mdr1 (vide supra) contains an AseI restriction site which overlaps with the encoded termination codon of AfuMDR1. The fragment is subjected to restriction enzyme digestion with AseI, and ligated to a DNA linker comprised of the annealed oligonucleotides TBN-78 (5'-TACCCATACGACGTCCCAGACTACGCTTGATAAT-3') (SEQ ID NO: 8) and TBN-79 (5'-CTAGATTATCAAGCG-TAGTCTGGGACGTCGTATGGG-3') (SEQ ID NO: 9). The DNA linker encodes the hemagglutanin flu epitope tag YPYDVPDYA. The resultant DNA fragment is subjected to restriction enzyme digestion with XbaI and subjected to agarose gel electrophoresis. The desired approximately 4100 base pair BamHI-XbaI DNA fragment encoding the Afu-mdr1/HA fusion is isolated by excising that portion of the agarose gel containing the fragment and electroeluting the DNA using a Centriluter™ Micro-electroeluter (Amicon, Inc.) according to the manufacturer's instructions. The resultant approximately 4100 base pair BamHI-XbaI DNA fragment is ligated to BamHI and XbaI-digested plasmid pYES2 vector DNA (Invitrogen Corp., San Diego, Calif.). The resultant plasmid, pPSM40, is useful for the expression of the AfuMDR1/HA in *Saccharomyces cerevisiae*. A representation of plasmid pPSM40 is provided as FIG. 4.

EXAMPLE 5

Expression of the AfuMDR1 gene in Baculovirus Systems

The desired approximately 4100 base pair BamHI-XbaI DNA fragment encoding Afu-mdr1 cDNA is prepared via the polymerase chain reaction and purified as described in Example 3 (vide supra). The approximately 4100 base pair BamHI-XbaI DNA fragment is ligated to BamHI-XbaI digested plasmid pFASTBAc-1 (GibcoBRL/Life Technologies, Gaithersburg, Md.). The resultant plasmid, pPSM43, is useful for the expression of AfuMDR1 in the BAC-TO-BAC™ Baculovirus Expression System (Gibco-BRL/Life Technologies). A restriction map and function map of plasmid pFASTBAc-1 is provided on page 5 of the GibcoBRL/Life Technologies Catalog Number 10359-016 (Instruction Manual—BAC-TO-BAC™ Baculovirus Expression System). The catalogue is herein incorporated by reference.

Figure 5:
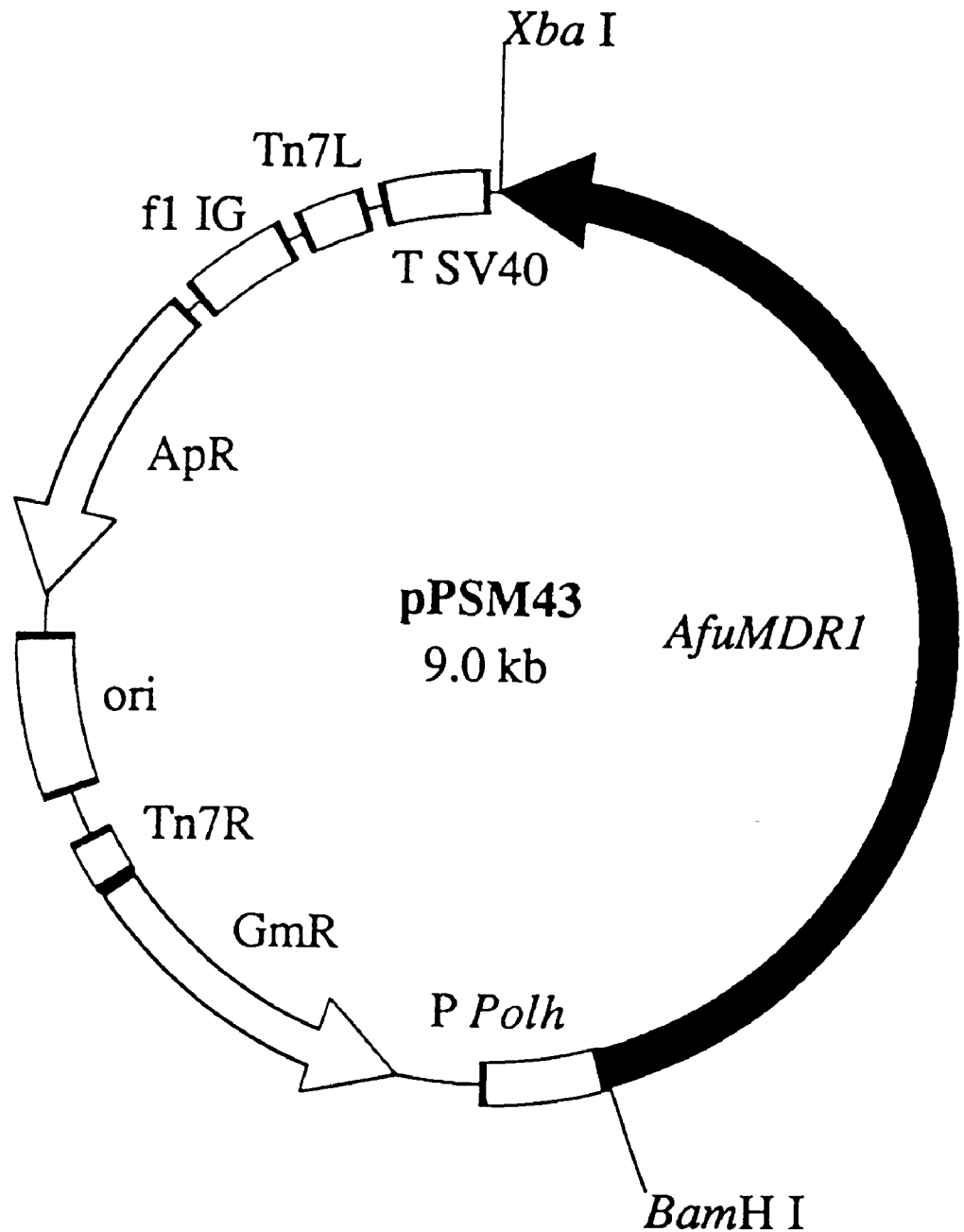
FIG. 5—A restriction enzyme site and function map of plasmid pPSM43.
Figure 6:
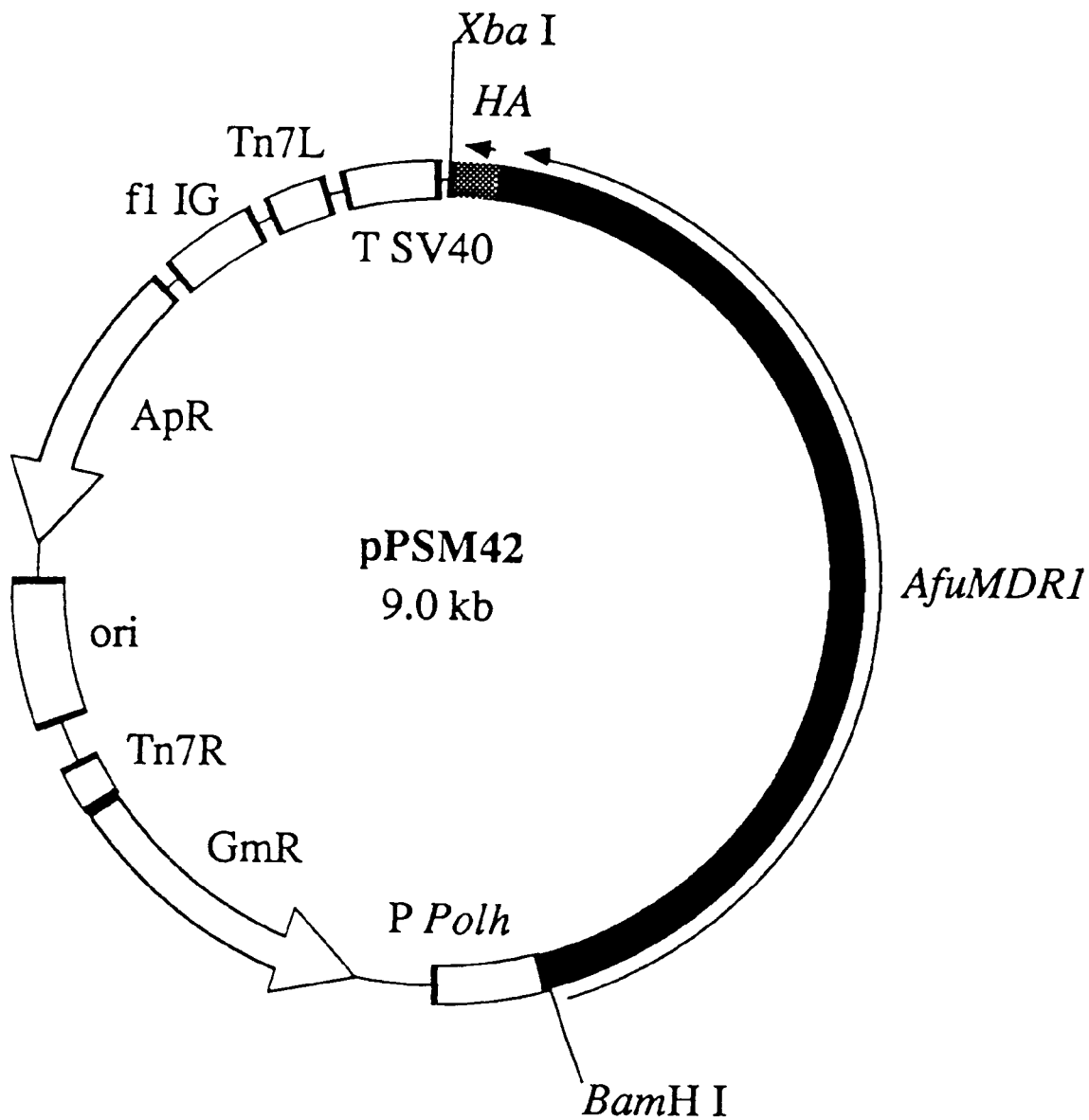
FIG. 6—A restriction enzyme site and function map of plasmid pPSM42.

A representation of plasmid pPSM43 is provided as FIG. 5. This plasmid contains the Afumdr1-encoding DNA operably linked to the polyhedrin promoter ($P_{polh}$) of the *Autographa californica* nuclear polyhedrosis virus (AcNPV). Plasmid pPSM43 also comprises a simian virus 40 (SV40) poly(A) transcription terminator located in a position 3' to the AfuMDR1 encoding DNA.

Transposition of pPSM43 into DH10Bac10 is conducted in accordance with the teachings of page 8 of GibcoBRL/Life Technologies Catalog Number 10359-016. Competent cells are provided as part of the expression kit accompanying pFASTBAC-1 in Catalog Number 10359-016.

Isolation of recombinant Bacmid DNA is accomplished in accordance with the teachings of pages 8 and 9 of GibcoBRL/Life Technologies Catalog Number 10359-016.

Transfection of *Spodoptera frugiperda* (Sf9) cells (ATCC #CRL 1711) with recombinant Bacmid DNA, harvest, and storage of the recombinant Baculovirus, and infection of insect cells with recombinant Baculovirus particles is accomplished in accordance with the teachings of pages 9 and 10 of GibcoBRL/Life Technologies Catalog Number 10359-016.

EXAMPLE 6

Expression of the AfuMDR1/HA fusion in Baculovirus Systems

The desired approximately 4100 base pair BamHI-XbaI cDNA fragment encoding the Afu-mdr1/HA fusion (see Example 3) is ligated to BamHI-XbaI digested plasmid pFASTBAc-1 (GibcoBRL/Life Technologies, Gaithersburg, Md.). The resultant plasmid, pPSM42 (illustrated in FIG. 6), is useful for the expression of Afu-mdr1/HA fusion in the BAC-TO-BAC™ Baculovirus Expression System (Gibco-BRL/Life Technologies), in substantial accordance with the methods as described above.

EXAMPLE 7

Antifungal Potentiator Assay Using *Saccharomyces cerevisiae*

Approximately $1 \times 10^6$ cells of a *Saccharomyces cerevisiae* INVSc1/pPSM41 culture are delivered to each of several agar plates containing YNB/CSM-Ura/gal. The agar surface is allowed to dry in a biohazard hood. *Saccharomyces cerevisiae* INVSc1/pPSM41 cells express the AfuMDR1 activity.

An antifungal compound that the untransformed yeast cell is typically sensitive to, such as R106I (U.S. Pat. No. 5,057,493, which is hereby incorporated herein by reference), is dissolved in 100% ethanol at a concentration of either 1 or 7 mg/ml. Twenty µl of the 1 mg/ml solution is delivered to an antibiotic susceptibility test disc (Difco Laboratories, Detroit, Mich.). After addition of the antifungal solution the disc is allowed to air dry in a biohazard hood. When dry, the disc is placed on the surface of the petri plates containing the *Saccharomyces cerevisiae* INVSc1/pPSM41 cells.

Compounds to be tested for the ability to inhibit AfuMDR1 are dissolved in dimethylsulfoxide (DMSO). The amount of compound added to the DMSO depends on the solubility of the individual compound to be tested. Twenty µl of the suspensions containing a compound to be tested are delivered to an antibiotic susceptibility test disc (Difco Laboratories, Detroit, Mich.). The disc is then placed on the surface of the dried petri plates containing the *Saccharomyces cerevisiae* INVSc1/pPSM41 cells approximately 2 cm from the antifungal-containing disc. Petri plates containing the two discs are incubated at 28° C. for about 16–48 hours.

Following this incubation period, the petri plates are examined for zones of growth inhibition around the discs. A zone of growth inhibition near the antifungal disc on the test plate indicates that the compound being tested for MDR inhibition activity blocks the activity of AfuMDR1 and allows the antifungal compound to inhibit the growth of the yeast host cell. Such compounds are said to possess MDR inhibition activity. Little or no zone of growth inhibition indicates that the test compound does not block MDR activity and, thus, AfuMDR1 is allowed to act upon the antifungal compound to prevent its activity upon the host cell.

EXAMPLE 8

Approximately one million cells of *Aspergillus montevidensis*, transformed with pPSM32, are delivered to the surface of several agar plates containing a rich growth medium. These cells express AfuMDR1. Assessment of anti-fungal potentiator activity of a battery of compounds is then performed as stated in Example 7.

We claim:

1. A method for determining the fungal multiple drug resistance inhibition activity of a compound which comprises:
   a) placing cultured fungal cells, transformed with a vector which expresses a nucleic acid encoding a protein having the amino acid sequence of SEO ID NO:2 in the presence of:
      (i) an antifungal agent to which said cultured fungal cells are resistant in their transformed state, but to which said cultured fungal cells are sensitive in their untransformed state; and
      (ii) a compound suspected of possessing *Aspergillus fumigatus* multiple drug resistance inhibition activity; and
   b) determining the fungal multiple drug resistance inhibition activity of said compound by measuring the ability of the antifungal agent to inhibit the growth of said cultured fungal cells.

2. The method of claim 1 wherein the cultured fungal cells are *Saccharomyces cerevisiae* cells.

3. An isolated nucleic acid molecule comprising a nucleotide sequence encoding a protein having the amino acid sequence of SEQ ID NO:2.

4. The isolated nucleic acid molecule of claim 3 comprising the nucleotide sequence of SEQ ID NO:1.

5. The isolated nucleic acid molecule of claim 3 comprising the nucleotide sequence of SEQ ID NO:3.

6. A vector comprising an isolated nucleic acid molecule encoding a protein having the amino acid sequence of SEQ ID NO:2.

7. The vector of claim 6, wherein the isolated nucleic acid molecule comprises the nucleotide sequence of SEQ ID NO:1.

8. The vector of claim 7, wherein the vector is pPSM41, pPSM40, pPSM43, or pPSM42.

9. The vector of claim 6, wherein the isolated nucleic acid molecule comprises the nucleotide sequence of SEQ ID NO:3.

10. The vector of claim 9, wherein the vector is pPSM6.

11. The vector of claim 9, further comprising a nucleic acid molecule that expresses hygromycin B phosphotransferase under control of an amdS promoter of *Aspergillus nidulans*.

12. A method of constructing a transformed host cell expressing a nucleic acid encoding a protein having the amino acid sequence of SEQ ID NO:2, the method comprising transforming a host cell with a recombinant DNA vector comprising an isolated nucleic acid encoding said protein.

13. A method of producing a protein having the amino acid sequence of SEQ ID NO:2 in a transformed host cell, the method comprising culturing a transformed host cell expressing a nucleic acid encoding said protein, said transformed host cell made by the method of claim 12, under conditions suitable for gene expression.

14. A transformed host cell comprising a vector, the vector comprising an isolated nucleic acid molecule encoding a protein having the amino acid sequence of SEQ ID NO:2.

15. The transformed host cell of claim 14, wherein the vector comprises an isolated nucleic acid molecule having the nucleotide sequence of SEQ ID NO:1 or SEQ ID NO:3.

16. The transformed host cell of claim 14, wherein the vector is pPSM41, pPSM40, pPSM43, pPSM42, or pPSM6.

* * * * *